United States Patent [19] [11] Patent Number: 4,996,139
Masukawa et al. [45] Date of Patent: Feb. 26, 1991

[54] SILVER HALIDE PHOTOGRAPHIC LIGHT-SENSITIVE MATERIAL CONTAINING NOVEL CYAN COUPLER

[75] Inventors: Toyoaki Masukawa; Takashi Uchida; Noritaka Nakayama, all of Hino, Japan

[73] Assignee: Konica Corporation, Tokyo, Japan

[21] Appl. No.: 388,168

[22] Filed: Aug. 1, 1989

[30] Foreign Application Priority Data

Aug. 12, 1988 [JP] Japan ................. 63-202270

[51] Int. Cl.$^5$ .................. G03C 7/32; G03C 1/10
[52] U.S. Cl. ......................... 430/558; 430/384; 430/385
[58] Field of Search .................. 430/384, 385, 558

[56] References Cited

U.S. PATENT DOCUMENTS 4,818,672  4/1989  Masukawa et al. ............. 430/558

Primary Examiner—Paul R. Michl
Assistant Examiner—Janet C. Baxter
Attorney, Agent, or Firm—Jordan B. Bierman

[57] ABSTRACT

A silver halide color photographic light-sensitive material is disclosed, which has a silver halide emulsion layer containing a novel cyan coupler represented by the following Formula I:

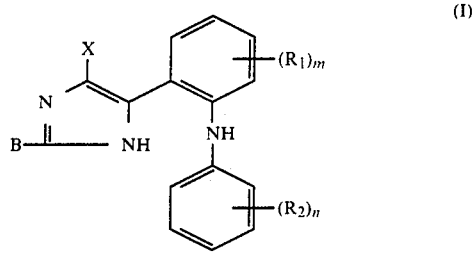

wherein B is an organic group comprising a carbon atom, nitrogen atom, oxygen atom or sulfur atom directly bonded to the imidazole ring; $R_1$ and $R_2$ each are a substituent; m is an integer of 0 to 4, n is an integer of 0 to 5, provided that the $R_1$S or $R_2$S each may be the same with or different from each other when m or n is 2 or more; and X is a group capable of being split off upon coupling reaction with the oxidation product of a color developing agent.

6 Claims, No Drawings

SILVER HALIDE PHOTOGRAPHIC LIGHT-SENSITIVE MATERIAL CONTAINING NOVEL CYAN COUPLER

FIELD OF THE INVENTION

The present invention relates to a silver halide photographic light-sensitive material containing a novel cyan coupler.

BACKGROUND OF THE INVENTION

Phenols or naphthols have been hitherto widely used as cyan couplers used in silver halide photographic light-sensitive materials. These are described, for example, in U.S. Pat. No. 2,369,929 and No. 2,474,293.

Cyan dye images obtained from the phenols or naphthols, however, have involved great problems in color reproduction. Namely, these cyan color-forming dyes have a poor sharpness at the shortwave side of the absorption spectrum, and also have unwanted absorption at the green portion, as well as at the blue portion in part. In the instances of color photographic papers or color reversal light-sensitive materials, there is no appropriate means for compensating them, making, in the recent circumstances, considerably poor the color reproducibility.

The present invention have now proposed novel cyan couplers, as disclosed in European Patent Application No. 249,453 and Japanese Patent Publication Open to Public Inspection (hereinafter referred to as Japanese Patent O.P.I. Publication) No. 226653/1988. In these couplers, the cyan dyes formed have superior spectral absorption characteristics as compared with conventional phenol and naphthol type cyan couplers, bringing about a great improvement in the color reproducibility. They also have a high molar absorptivity of the color-forming dyes, and have made it possible to greatly decrease silver weight as compared with conventional couplers. However, the resulting dye images may have an insufficient fastness, and accordingly it has been sought to newly provide a cyan coupler capable of forming a dye image having a much higher fastness.

SUMMARY OF THE INVENTION

An object of the present invention is to provide a silver halide photographic light-sensitive material that contains a cyan coupler capable of forming a cyan dye having a superior color reproducibility and sufficient fastness, and capable of giving a high color-forming density.

The above object can be achieved by a silver halide photographic light-sensitive material, comprising a support and provided thereon a silver halide emulsion layer containing a cyan coupler represented by the following Formula I.

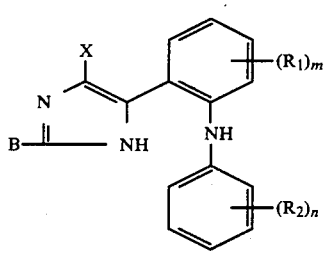

(I)

wherein B is an organic group comprising a carbon atom, nitrogen atom, oxygen atom or sulfur atom directly bonded to the imidazole ring; $R_1$ and $R_2$ each are a substituent; m is an integer of 0 to 4, and n is an integer of 0 to 5, provided that the groups represented by said $R_1$ and $R_2$ are respectively allowed to be the same with or different from each other when m or n is 2 or more; and X is a group capable of being split off upon coupling reaction with the oxidized product of a color developing agent.

DETAILED DESCRIPTION OF THE INVENTION

In the above Formula (I), the organic group represented by B, comprising a carbon atom directly bonded to the imidazole ring, includes an alkyl group as exemplified by methyl, i-propyl, t-butyl, trifluoromethyl, benzyl, 3-(4-aminophenyl)propyl, allyl, 2-dodecyloxyethyl, 3-phenoxypropyl, 2-hexylsulfonylethyl, 3-[4-(4-dodecyloxybenzene)sulfonamidophenyl]propyl, 1-methyl-2-[(2-octyloxy-5-t-octylphenyl)sulfonamidophenyl]ethyl, 1-methyl-2-[2-octyloxy-5-(2-octyloxy-5-t-octylphenylsulfonamido) phenylsulfonamido]ethyl or 2-](2-octyloxy-5-(2-octyloxy-5-t-octylphenylsulfonamido)pheynsulfonamido]ethyl, an aryl group as exemplified by phenyl, naphthyl, 2,4-dichlorophenyl, 2-hydroxy-5-methylphenyl, 2-acetamidophenyl, 2-methanesulfonamidophenyl, 2-butaneamidophenyl, 2-(N,N-dimethylsulphamoylamino)phenyl, 2-(4-dodecyloxybenzenesulfonamido)phenyl, 2-[2-(2,4-di-t-amylphenoxy)hexaneamido]phenyl, 2-(2-octyloxy-5-t-octylphenylsulfonamido)phenyl, 4-carbamoylphenyl, 4-cyanophenyl, 4-carboxyphenyl or 4-ethyoxycarbonylphenyl, a heterocyclic group as exemplified by 4-pyridyl or 2-benzoimidazolyl, a cyano group, a carboxyl group, an acyl group, a carbamoyl group, an alkoxycarbonyl group, and an aryloxycarbonyl group.

The organic group comprising a nitrogen atom directly bonded to the imidazole ring includes an acylamino group as exemplified by acetamido, benzamido, 2,4-di-t-amylphenoxyacetamido or 2,4-dichlorobenzamido, an alkoxycarbonylamino group as exemplified by methoxycarbonylamino, propoxycarbonylamino or t-butoxycarbonyl amino, an aryloxycarbonylamino group as exemplified by phenoxycarbonylamino, a sulfonamido group as exemplified by methanesulfonamido, octanesulfonamido, benzenesulfonamido or 4-dodecyloxybenzenesulfonamido, an anilino group as exemplified by phenylamino, 2-chlororanilino or 2-chloro-4-tetradecanamidoanilino, a ureido group as exemplified by N-methylureido, N-butylureido, N-phenylureido or N,N-dibutylureido, a sulfamoylamino group as exemplified by N,N-diethylsulfamoylamino or N-phenylsulfamoylamino, an amino group as exemplified by unsubstituted amino, N-methylamino or N,N-diemthylamino, and a heterocyclic group as exemplified by 2,4-dimethyl-1-pyroazolyl or 2,6-diemthylmorpholino.

The organic group comprising an oxygen atom directly bonded to the imidazole ring includes an alkoxy group as exemplified by methoxy, ethoxy, i-propoxy, butoxy, 2,2,2,-trifluoroethoxy, 3,3,3-trifluoropropoxy, 2-chloroethoxy, 2-cyanoethoxy or 2-butanesulfonylethoxy, an aryloxy group as exemplified by phenoxy, 4-methoxyphenoxy, 2,4-dichlorophenoxy or 4(2-ethylhexanamido)phenoxy, a silyloxy group as exemplified by trimethylsilyloxy, dimethylphenyllsilyloxy or dimethyl-t-butylsilyloxy, and a heterocyclic oxy group as exemplified by tetrahydropyranyloxy, 3-pyridyloxy or 2(1,3-benzimidoazolyl)oxy.

The organic group comprising a sulfur atom directly bonded to the imidazole ring includes an alkylthio group as exemplified by methylthio, ethylthio, butylthio, 3-[4-(4-dodecyloxybenzene)sulfonamidophenyl]propylthio or 4-(2-butoxy-5-t-octylphenylsulfonamido)benzylthio, an arylthio group as exemplified by phenylthio, 2-naphthylthio, 2,5-dichlorophenylthio, 4-dodecylphenylthio or 2-butoxy-5-t-octylphenylthio, a heterocyclic thio group as exemplified by 2-pyridylthio, 2-(1,3-benzoxazolyl)thio, 1-hexadecyl-1,2,3,4-tetrazolyl-5-thio or 1-(3-N-octadecylcarbamoyl)phenyl-1,2,3,4-tetrazolyl-5-thio.

There are no particular limitations on the substituent represented by $R_1$ and $R_2$ each, but it may include, for example, a halogen atom, and groups such as cyano, nitro, carboxy, alkyl, alkoxy, carbamoyl, sulfamoyl, acyl, acyloxy, alkoxycarbonyl, alkylamido, arylamido, alkylsulfonamido, arylsulfanamido, dialkylcarbamoylamino, alkoxycarbonylamino, aryloxycarbonylamino, and sulfamoylamino.

Preferred as the alkyl group represented by $R_1$ and $R_2$ each is a straight-chain or branched alkyl group having 1 to 22 carbon atoms, including, for example, groups such as methyl, ethyl, butyl, and dodecyl. These alkyl groups also include a cycloalkyl group such as a cyclohexyl group or may be substituted. Preferred substituents include a halogen atoms, a hydroxy group, a carboxy group, a cyano group, a sulfo group, and an alkoxy group having 1 to 22 carbon atoms.

Preferred as the alkoxy group is a straight-chain or branched alkoxy group having 1 to 22 carbon atoms, including groups such as methoxy, ethoxy, i-propoxy, octyloxy, and dodecyloxy.

The carbamoyl group includes an unsubstituted alkylcarbamoyl group such as an ethylcarbamoyl or dodecylcarbamoyl group, and a substituted alkylcarbamoyl group such as a diethylcarbamoyl, butyloxypropylcarbamoyl or dodecyloxypropylcarbamoyl group.

The sulfamoyl group also similarly includes an unsubstituted alkylsulfamoyl group such as an ethylsulfamoyl, diethylsulfamoyl or dodecylsulfamoyl group, and a substituted alkylsulfamoyl group such as a dodecyloxypropylsulfamoyl group.

The arylcarbamoyl group includes a phenylcarbamoyl group and a substituted phenylcarbamoyl group. The arylsulfamoyl group includes a phenylsulfamoyl group and a variety of substituted phenylsulfamoyl groups.

There are also included an acyl group such as an acetyl, benzoyl, butanesulfonyl or benzenesulfonyl group, an acyloxy group such as an acetoxy, lauroyloxy or butanesulfonyloxy group, and an alkoxycarbonyl group such as an ethoxycarbonyl, i-propyloxycarbonyl or 2-ethylhexyloxycarbonyl group.

The alkylamido group includes a substituted or unsubstituted alkylamido group having 1 to 22 carbon atoms. Typical examples of an unsubstituted alkylamido group include an acetamido group, a butaneamido group, a laurylamido group, and a stearylamido group. It may also include an alicyclic amido group such as a cyclohexanecarbonamido group. It may also have a branched structure as exemplified by a 2-ethylhexanamido group or may contain an unsaturated bond.

A substituted alkylamido group of the above alkylamido group includes a halogen-substituted alkylamido group such as a monochloroacetamido, trichloroacetamido or perfluorobutanamido group, and a phenoxy-substituted alkylamido group such as a m-pentadecylphenoxyacetamido, α-(2,4-di-t-amylphenoxy)-pentanamido, α-(2,4-di-t-acylphenoxy)acetamido or o-chlorophenoxymyristic acid amido group.

The arylamido group also includes a substituted or unsubstituted arylamido group. It typically includes an unsubstituted arylamido group such as a benzamido or naphthamido group, and a substituted arylamido group also typically includes an alkyl-substituted benazmido group such as a p-t-butylbenzamido or p-methylbenzamido group, an alkoxy-substituted benzamido group such as a p-methoxybenzamido or o-dodecyloxybenzamido group, an amido-substituted benzamido group such as a p-acetamidobenzamido, m-lauroylamidobenzamido or m-(2,4-di-t-amylphenoxyacetamido)benzamido group such as an o-hexadecanesulfonamidobenzamido or p-butanesulfonamidobenzamido group.

The alkoxycarbonylamino group includes a substituted or unsubstituted alkoxycarbonylamino group having 1 to 22 carbon atoms. It typically includes groups such as ethoxycarbonylamino, i-propoxycarbonylamino, octyloxycarbonylamino, decyloxycarbonylamino, and methoxyethoxycarbonylamino. The aryloxycarbonyl group typically includes a phenoxycarbonyl group.

The dialkylcarbamoylamino group typically includes groups such as dimethylcarbamoylamino and diethylcarbamoylamino.

The alkylsulfonamido group includes an unsubstituted alkylsulfonamido group having 1 to 22 carbon atoms, such as a methanesulfonamido, butanesulfonamido or dodecanesulfonamido group, and a substituted alkylsulfonamido group such as a benzylsulfonamido group.

The arylsulfonamido group includes an unsubstituted arylsulfonamido group such as a benzenesulfonamido or naphthalenesulfonamido group, or a substituted arylsulfonamido group including an alkyl-substituted benzenesulfonamido group such as a p-toluenesulfonamido, 2,4,6-trimethylbenzenesulfonamido or p-dodecylbenzenesulfonamido group, and an alkoxy-substituted benzensulfonamido group such as a p-dodecyloxybenzenesulfonamido or butyloxybenzenesulfonamido group.

A typical example of the sulfamoylamino group preferably includes a dialkylsulfamoylamino group such as a dimethylsulfamoylamino or dibutylsulfamoylamino group.

The group represented by X, capable of being split off upon coupling reaction with an oxidized product of a color developing agent, includes a halogen atom such as chlorine, bromine or flourine, and groups such as hydroxyl, alkoxy, aryloxy, heterocylic oxy, acyloxy, sulfonyloxy, alkoxycarbonyloxy, aryloxycarbonyl, alkyloxyalkyloxy, alkoxyoxalyloxy, alkylthio, mercapto, arylthio, heterocyclic thio, alkoxythiocarbonylthio, acylamino, substituted amino, nitrogen-containing heterocylic ring combined with a nitrogen atom, sulfonamido, alkyloxycarbonylamino, aryloxycarbonylamino, and carboxyl. Halogen atom, particularly chlorine atom, is preferable.

Of the compound represented by Formula (I), ones each having a group of:

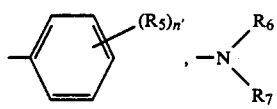

or —LR$_8$ as the group represented by B, namely, represented by Formula (II), (III) and (IV), are preferably used.

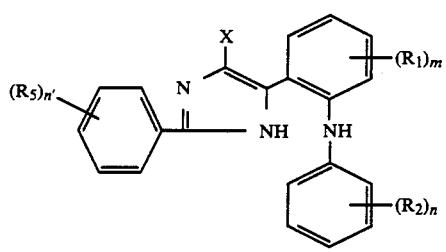

Formula (II)

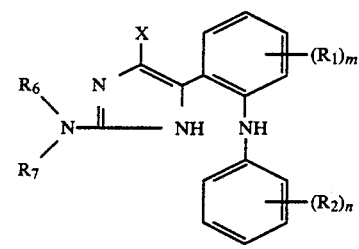

Formula (III)

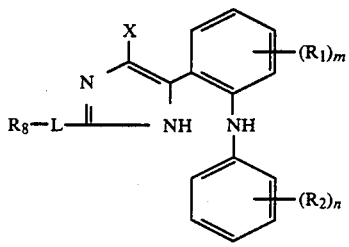

Formula (IV)

In Formula (II) to (IV), R$_1$, R$_2$, X, m and n have the same definitions as R$_1$, R$_2$, X, m and n in the above Formula (I): R$_5$, R$_6$, R$_7$ and R$_8$ each represent a substituent; L represents an oxygen atom or a sulfur atom; and n' represents an integer of 0 to 5. R$_5$ may represent different two or more groups when n' is two or more.

Of the compound represented by Formula (II), a still preferred compound includes the compound represented by the following Formula (V), namely, having a

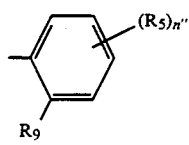

group as the group represented by B.

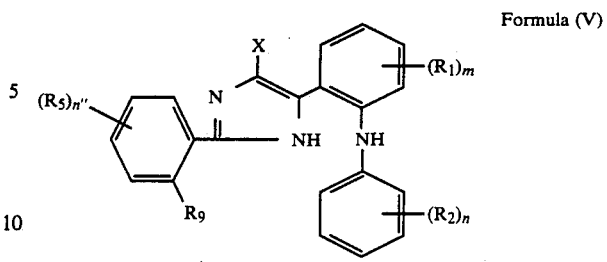

Formula (V)

In Formula (V), R$_1$, R$_2$, R$_5$, X, m and n have the same definitions as R$_1$, R$_2$, R$_5$, X, m and n in the above Formula (II). n is an integer of zero to 4. R$_9$ represents an amino group, alkylamino group, an arylamino group, an an arylamido group, an alkylsulfonamido group, an arylsulfonamido group, a dialkylcarbamoyl group, an alkoxycarbonylamino group, an aryloxycarbonylamino group or a sulfamoylamino group.

An alkyl group contained in the alkylamino group represented by R$_9$ may preferably include a straight-chain or branched alkyl group having 1 to 32 carbon atoms, also including a cycloalkyl group such as a cyclohexyl group. These alkyl groups may also be substituted. Preferred substituents typically include a halogen atom, a hydroxyl group, a carboxyl group, a cyano group, a sulfo group, and an alkoxy group having 1 to 22 carbon atoms.

An aryl group contained in the arylamino group represented by R$_9$ may preferably include a phenyl group. The phenyl group may be substituted with a nitro group, an amido group, a sulfonamido group, or the like.

In instances in which —R$_9$ is an alkylamido group, an arylamido group, an alkoxycarbonylamino group, an aryloxycarbonylamino group, a dialkylcarbamoylamino group, an alkylsulfonamido group or an arylsulfonamido group, these groups are the same as the groups represented by R$_1$ and R$_2$ in Formula I.

In Formula (III), the alkyl group and aryl group each represented by R$_6$ and R$_7$ specifically include the alkyl group and aryl group described for R$_9$ in the above Formula (V).

The heterocyclic ring formed by combination of R$_6$ with R$_7$ may preferably include a heterocyclic ring of 5 or 6 members. These heterocyclic rings may have a substituent, or may further be condensed with a carbon ring.

In Formula (IV), R$_8$ represents a hydrogen atom, an alkyl group, an aryl group or a heterocyclic group. The alkyl group and aryl group each represented by R$_8$ specifically include the alkyl group and aryl group described for R$_9$ in the above Formula (V).

The heterocyclic group represented by R$_8$ may preferably include a heterocyclic group of 5 to 6 members, specifically including groups such as 2-pyridyl, 4-pyridyl, 2-benzimidazolyl, 3,5-dimethyl-1-pyrazolyl, 4-pyridyl, 2-benzimidoazolyl, 3,5-dimethyl-1-pyrazolyl, 4-morpholino, 3,5-dimethyl-2furyl, 2,4-dimethyl-5-thiazolyl, and 2-acetamido-4-methyl-5-pyrimidinyl.

Typical examples of the cyan coupler used in the present invention are shown below, but the present invention is by no means limited by these.

| No. | X | B | R₁ | R₂ | m | n |
|---|---|---|---|---|---|---|
| 1 | H | phenyl | 5-NHCOCH₂O-（2-C₅H₁₁(t), 4-C₅H₁₁(t)-phenyl) | — | 1 | 0 |
| 2 | Cl | phenyl | 5-NHCOCH₂O-（2-C₅H₁₁(t), 4-C₅H₁₁(t)-phenyl) | — | 1 | 0 |
| 3 | Cl | phenyl | 5-NHCOCH₂O-（2-C₅H₁₁(t), 4-C₅H₁₁(t)-phenyl) | 2'-Br, 4'-Br | 1 | 2 |
| 4 | H | 2-(NHCOCH(C₃H₇(i))O-（2-C₅H₁₁(t), 4-C₅H₁₁(t)-phenyl))-phenyl | — | — | 0 | 0 |
| 5 | Cl | 2-(NHCOCH(C₃H₇(i))O-（2-C₅H₁₁(t), 4-C₅H₁₁(t)-phenyl))-phenyl | — | — | 0 | 0 |

-continued

[Structure: aniline-substituted coupler with $(R_1)_m$ on one ring, $(R_2)_n$ on another, with X, N-B, NH groups]

| No. | X | B | $R_1$ | $R_2$ | m | n |
|---|---|---|---|---|---|---|
| 6 | H | NHCOCHCH$_2$SO$_2$C$_{12}$H$_{25}$ with CH$_3$ and o-tolyl | — | — | 0 | 0 |
| 7 | Cl | NHCOCHCH$_2$SO$_2$C$_{12}$H$_{25}$ with CH$_3$ and o-tolyl | — | — | 0 | 0 |
| 8 | H | 4-(OC$_{12}$H$_{25}$)phenyl-NHSO$_2$-o-tolyl | 5-NHCOCF$_3$ | — | 1 | 0 |
| 9 | H | 2-C$_8$H$_{17}$-4-OC$_4$H$_9$-phenyl-NHSO$_2$-o-tolyl | 5-NHCOCH$_3$ | — | 1 | 0 |
| 10 | Cl | 2-C$_8$H$_{17}$-4-OC$_8$H$_{17}$-phenyl-NHSO$_2$-o-tolyl | 4-NHCOCHO-C$_3$H$_7$(i) with 2-C$_5$H$_{11}$ and 4-C$_5$H$_{11}$ | — | 1 | 0 |

-continued

| No. | X | B | R₁ | R₂ | m | n |
|---|---|---|---|---|---|---|
| 11 | Cl | 2-methylphenyl-NHSO₂C₁₆H₃₃ | 5-NHCOC₃H₇(i) | — | 1 | 0 |
| 12 | Cl | 2-methylphenyl-NHCOCHO-C₄H₉ with 2,5-di(C₅H₁₁(t)) substitution | 5-NHCOC₃H₇(i) | 4'-OCH₃ | 1 | 1 |
| 13 | Cl | 2-methylphenyl-NHSO₂N(CH₃)₂ | 5-NHCOCHO-C₄H₉ (with C₅H₁₁(t) substitution) | 4'-CH₃ | 1 | 1 |
| 14 | $\begin{array}{c}N=N\\ \|\quad\|\\ N\quad N-C_6H_5\\ \diagdown\!\diagup\\ C\\ \|\\ S-\end{array}$ | phenyl-NHCO | 5-NHCO-(2-OC₁₄H₂₉-phenyl) | — | 1 | 0 |
| 15 | H | 2-methylphenyl-NHCOOCH₂CHC₄H₉ (C₂H₅) | 5-NHCOOCH₂SO₂C₁₈H₃₇ (with CH₃, CH₃) | — | 1 | 0 |

-continued

| No. | X | B | R₁ | R₂ | m | n |
|---|---|---|---|---|---|---|
| 16 | H | NHCOOC₃H₇(i) — (o-tolyl) | 5-NHSO₂C₁₆H₃₃ | — | 1 | 0 |
| 17 | H | NHCOOC₂H₅ — (o-tolyl) | 5-NHCOCHC₃H₇ with 2,4-di(C₅H₁₁(t)) phenyl | — | 1 | 0 |
| 18 | Cl | NHCOOC₂H₅ — (o-tolyl) | 5-NHCOCHC₃H₇(i) with 2,4-di(C₅H₁₁(t)) phenyl | — | 1 | 0 |
| 19 | Cl | NHCON(CH₃)₂ — (o-tolyl) | 5-NHCOCHC₂H₅ with 3-C₁₅H₃₁ phenyl | 3'-CH₃ | 1 | 1 |
| 20 | Cl | NHCOCF₃ — (o-tolyl) | 5-NHCOOCH₂CHC₄H₉ / C₂H₅ | — | 1 | 0 |

-continued

General structure: B-C(=N)-C(X)=... attached to aniline with (R₁)ₘ on one ring and -NH- linking to another ring with (R₂)ₙ

| No. | X | B | R₁ | R₂ | m | n |
|---|---|---|---|---|---|---|
| 21 | Cl | 2-methylphenyl-NHCO- (pentafluorophenyl amide) | — | 4'-NHCOCH₃ | 1 | 1 |
| 22 | H | CH₃O— | 5-NHCOCHO-C₄H₉ / 2-C₅H₁₁(t), 4-C₅H₁₁(t) phenyl | 4'-NHCOCH(C₃H₇(i)) with 2-C₅H₁₁(t),4-C₅H₁₁(t) phenyl | 0 | 1 |
| 23 | Cl | CH₃O— | 5-NHCOCHO-C₄H₉ / 2-C₅H₁₁(t),4-C₅H₁₁(t) phenyl | 2'-Cl, 4'-Cl | 1 | 2 |
| 24 | H | 4-CONH₂-phenyl | — | 4'-NHCOCH(C₄H₉) with 2-C₅H₁₁(t),4-C₅H₁₁(t) phenyl | 0 | 1 |
| 25 | H | 3-NO₂-phenyl | — | 4'-NHCOCH(C₄H₉) with 2-C₅H₁₁(t),4-C₅H₁₁(t) phenyl | 0 | 1 |

-continued

| No. | X | B | $R_1$ | $R_2$ | m | n |
|---|---|---|---|---|---|---|
| 26 | Cl | 4-methylphenyl-OCH₃ | 5-NHCOCHCH₂SO₂C₁₂H₂₅ / CH₃ | — | 1 | 0 |
| 27 | H | 2-chloro-methylphenyl | 5-NHCOCHO-C₃H₇(i), 2-C₅H₁₁(t), 4-C₅H₁₁(t) phenyl | 2'-Br, 4'-Br | 1 | 2 |
| 28 | H | 4-NC-methylphenyl | 5-NHCOCHO-C₃H₇(i), 2-C₅H₁₁(t), 4-C₅H₁₁(t) phenyl | 2'-Br, 4'-Br | 1 | 2 |
| 29 | H | 3-methylpyridyl | 5-NHCOCHO-C₃H₇(i), 2-C₅H₁₁(t), 4-C₅H₁₁(t) phenyl | — | 1 | 0 |
| 30 | H | 3,5-dimethylpyrazolyl | 5-NHCOCHO-C₃H₇(i), 2-C₅H₁₁(t), 4-C₅H₁₁(t) phenyl | 2'-Br, 4'-Br | 1 | 2 |

-continued

Structure:

$$\text{X-C(=N-B)-... with NH-phenyl}(R_1)_m(R_2)_n$$

| No. | X | B | R₁ | R₂ | m | n |
|---|---|---|---|---|---|---|
| 31 | H | morpholine with 2,6-diCH₃ | 5-NHCOCHO-C₄H₉ phenyl with 2-C₅H₁₁(t), 4-C₅H₁₁(t) | — | 1 | 0 |
| 32 | H | pyrazole (CH₃, C₂H₅, CH₃) | 5-NHCOCHO-C₃H₇(i) phenyl with 2-C₅H₁₁(t), 4-C₅H₁₁(t) | — | 1 | 0 |
| 33 | Cl | pyrazole (CH₃, CH₃, CH₃) | 5-NHCOCHO-C₃H₇(i) phenyl with 2-C₅H₁₁, 4-C₅H₁₁ | — | 1 | 0 |
| 34 | H | pyrazole (CH₃, CH₃, CH₃) | 5-NHCOCHO-C₃H₇(i) phenyl with 2-C₅H₁₁(t), 4-C₅H₁₁(t) | — | 1 | 0 |
| 35 | Cl | pyrazole (CH₃, CH₃, CH₃) | 5-NHCOCHO-C₃H₇(i) phenyl with 2-C₅H₁₁(t), 4-C₅H₁₁(t) | — | 1 | 0 |

-continued

| No. | X | B | $R_1$ | $R_2$ | m | n |
|---|---|---|---|---|---|---|
| 36 | Cl | 3,5-dimethylpyrazol-1-yl | ![phenyl] | 4'-NHCOCHO(C4H9)- with 2-C5H11(t), 5-C5H11(t) | 1 | 1 |
| 37 | Cl | 3,5-dimethylpyrazol-1-yl | 5-NHSO2C4H9 | 4'-NHCOCHO(C3H7(i))- with 2-C5H11(t), 5-C5H11(t) | 1 | 1 |
| 38 | Cl | 3,5-dimethylpyrazol-1-yl | 5-NHSO2- (2-OC8H17, 5-C8H17 phenyl) | 4'-CH3 | 1 | 1 |
| 39 | H | 2,4-dichloroanilino | 5-NHCOCHO(C3H7(i))- with 2-C5H11(t), 5-C5H11(t) | — | 1 | 0 |
| 40 | H | 2-trifluoromethylanilino | 5-NHCOCHO(C3H7(i))- with 2-C5H11(t), 5-C5H11(t) | — | 1 | 0 |

-continued

| No. | X | B | R₁ | R₂ | m | n |
|---|---|---|---|---|---|---|
| 41 | H | (t)C₈H₁₇NH— | 5-NHCOOCH₂CHC₄H₉<br>                     \|<br>                     C₂H₅ | — | 1 | 0 |
| 42 | Cl | C₁₆H₃₃S— | 5-NHCOOC₃H₇(i) | — | 1 | 0 |
| 43 | Cl | 2-Cl-C₆H₄-CH₂S— | 5-NHCOCHO-C₄H₉ / C₅H₁₁(t) (2,5-disubstituted phenyl) | — | 1 | 0 |
| 44 | Cl | CH₃SO₂NHCH₂CH₂S— | 5-NHCOC₂H₅ | 4'-NHCOC₁₁H₂₃ | 1 | 1 |
| 45 | Cl | (i)C₃H₇O— | 5-NHCOCHO-C₃H₇ / C₅H₁₁(t) | 4'-Cl | 1 | 1 |
| 46 | Cl | CH₃OCH₂CH(Cl)— | 5-NHCOCHO-C₃H₇ / C₅H₁₁(t) | 4'-Cl | 1 | 1 |
| 47 | Cl | ClCH₂— | 5-NHCOCHO-C₄H₉ / C₅H₁₁(t) | 2'-Cl<br>4'-Cl | 1 | 2 |

-continued

[Structure: central benzene ring (positions 3,4,5,6) with NH linking to a second benzene ring (positions 2',3',4',5',6'); substituents (R₁)ₘ and (R₂)ₙ; attached to CH=C(X)–N=B group]

| No. | X | B | R₁ | R₂ | m | n |
|---|---|---|---|---|---|---|
| 48 | Cl | C₁₆H₃₃S— | C₅H₁₁(t), C₅H₁₁(t), 5-NHCOCHO-C₄H₉ | 4'-NHCOC₂H₅ | 1 | 1 |
| 49 | H | 2,4,6-trichlorophenyl-S— | C₅H₁₁(t), C₅H₁₁(t), 5-NHCOCHO-C₄H₉ | 4'-NHCOCH₃ | 1 | 1 |
| 50 | H | 2-methyl-nitrobenzene (o-NO₂-tolyl) | C₅H₁₁(t), C₅H₁₁(t), 5-NHCOCHO-C₃H₇(i) | 2'-Br, 4'-Br | 1 | 2 |
| 51 | H | 2-methyl-aniline (o-NH₂-tolyl) | C₅H₁₁(t), C₅H₁₁(t), 5-NHCOCHO-C₃H₇(i) | — | 1 | 0 |
| 52 | H | 2-(OC₈H₁₇)-4-(C₈H₁₇)-phenyl-NHSO₂-(o-tolyl) | C₅H₁₁(t), C₅H₁₁(t), 5-NHCOCHO-C₃H₇(i) | — | 1 | 0 |

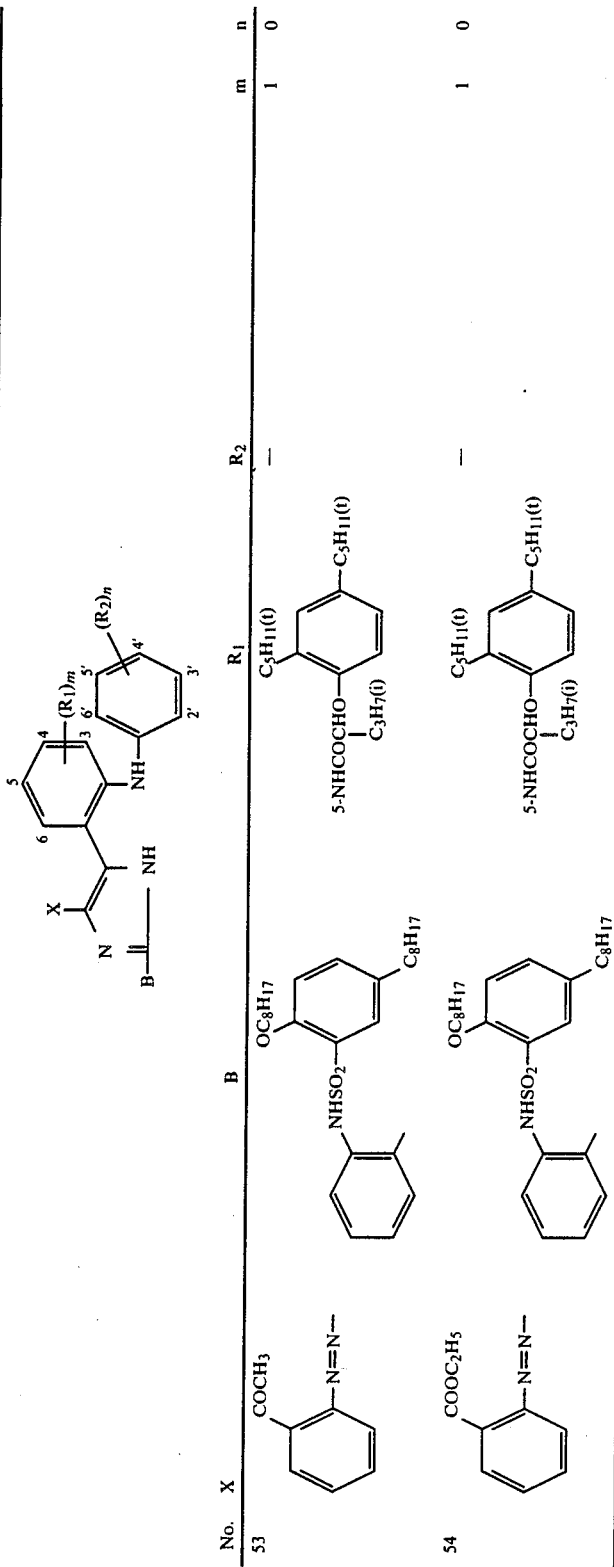

Typical examples for synthesizing the coupler of the present invention are described below.

SYNTHESIS EXAMPLE 1

(Synthesis of Exemplary Compound 30)

Synthesis of 2-chloro-5-nitroacetophenone

On a ice bath, 80 ml of fuming nitric acid (d=1.52) was cooled to 4° C., and 24.0 g of o-chloroacetophenone was dropwise added thereto at 4 to 7° C. taking about 3 hours. In the state as it stands, stirring was continued at 4° C. for 1 hour.

The reaction mixture was subsequently poured onto ice, and pale yellow crystals deposited were collected by filtration. The crystals were recrystallized from alcohol to obtain 22 g of 2-chloro-5-nitroacetophenone. m.p.: 59° to 61° C.

Synthesis of 2-acetyl-4-nitrodiphenylamine

Under heating at 125° C. to 135° C., 20 g of 2-chloro-5-nitroacetophenone, 20 g of aniline and 20 g of anhydrous potassium carbonate were stirred for 5 hours.

When cooled to about 80° C., 80 ml of alcohol was added and the reaction mixture was allowed to cool with stirring. After it was allowed to stand overnight in that state, yellowish brown crystals were deposited. The crystals were collected by filtration, washed with alcohol, and then washed with water. The resulting crude crystals were recrystallized from alcohol to obtain 11.0 g of 2-acetyl-4-nitrodiphenylamine. m.p.: 130° to 132° C.

Synthesis of 2-acetyl-4-{2-(2'-4'-di-t-amylphenoxy-i-pentanamido)}diphenylamine

In a mixture of 10.2 g of 2-acetyl-4-nitrodiphenylamine and 200 ml of alcohol, 0.5 g of a Pd-C catalyst was added to carry out catalytic reduction at normal pressure. In about 3 hours, 2.8 l of hydrogen was absorbed and the reaction stopped (theoretical quantity: 1.35 l). The reaction mixture turned thick yellow.

The catalyst was removed by filtration, and the filtrate was concentrated. The remaining yellowish brown oil was stood under a reduced pressure made by a vacuum pump for removing the remaining alcohol in the oil, which thus obtained oily substance was used for the next reaction as it was.

The oily substance previously mentioned was dissolved in 200 ml of acetonitrile, and then 4.0 g of pyridine was added. Into this mixture, poured was a solution obtained by dissolving 14.1 g of 2,4-di-t-amylphenoxy-i-pentanoylchloride in 50 ml of acetonitrile. Heat was generated and crystals were formed, which, however, were dissolved after a while as a result of stirring. The resulting solution was boiled and refluxed for 2 hours, and thereafter concentrated.

The remaining viscous substance was extracted with ethyl acetate, and the ethyl acetate layer was washed with diluted hydrochloric acid, and then washed with water, followed by dehydration with magnesium sulfate.

The ethyl acetate layer was concentrated, and the remaining oil was purified by column chromatography. There was obtained 22.0 g of a yellow amorphous solid.

Synthesis of Exemplary Compound 30

In 150 ml of chloroform, 11.1 g of 2-acetyl-4-{2-(2'-4'-di-t-amylphenoxy-i-pentanamido)}diphenylamine was dissolved. To the resulting solution, 9.85 g of bromine was dropwise added taking about 3 hours at room temperature. The reaction mixture was further maintained at room temperature for 30 minutes, and thereafter for 30 minutes at temperatures raised to 40° to 50° C., followed by concentration after completion of the reaction. The remaining yellowish brown oil was again dissolved in 200 ml of chloroform. In the resulting solution, a chloroform solution of 3,5-dimethylpyrazolecarboamidine* (prepared from 16.5 g of a nitrate thereof) was added with stirring, and the mixture was boiled and refluxed for 10 hours. Deposition of crystals followed. Since, however, the crystals were comprises of 3,5-dimethylpyrazolecarboamidine nitrate, they were removed by filtration after the reaction, and the resulting filtrate was concentrated. The remaining oil content was separated and purified by column chromatography, thus obtaining 13.4 g of Exemplary Compound 30 as an amorphous solid. *In 50 ml of water, 16.5 g of 3,5-dimethylpyrazolecarboamidine nitrate wa added and almost completely dissolved, followed by addition, with stirring, of a solution obtained by dissolving 33 g of potassium hydroxide in 50 ml of water. Free carboamidine, separated as an oil, was extracted with chloroform. The liquid chloroform extract was dehydrated using anhydrous magnesium sulfate, and the resulting solution was used in the react as it was.

Mass spectrometry confirmed that this product showed $M^+ = 818$ and had the structure as previously set out.

SYNTHESIS EXAMPLE 2

(Synthesis of Exemplary Compound 34)

In 5.92 of Exemplary Compound 30, 160 ml of alcohol, 1.82 g of triethylamine and also a Raney nickel catalyst, and the mixture was subjected to catalystic reduction at normal pressure for 32 hours. Formation of white precipitates followed with progress of the reaction. After the reaction was completed, the resulting white crystals were collected by filtration and then washed with alcohol. To separate them from the Raney nickel catalyst, the crystals obtained were treated with an aqueous diluted ammonium solution and extracted with ethyl acetate. The ethyl acetate layer was dehydrated with anhydrous magnesium sulfate, followed by concentration. The remaining grayish white solid was recrystallized from acetonitrile to obtain 2.4 g of Exemplary Compound 34.

m.p.: 184.5° to 186.5° C.

SYNTHESIS EXAMPLE 3

(Synthesis of Exemplary Compound 35)

In a mixture of 30 ml of ethyl acetate and 50 ml of dimethylformamide, 2.0 g of the above Exemplary Compound 34 was dissolved, to which 0.44 g of n-chlorosuccinimide was added, and then the reaction was carried out at room temperature for 3 days. The reaction product was poured onto water, and extracted with ethyl acetate. The resulting ethyl acetate layer was washed with water and thereafter dehydrated with anhydrous magnesium sulfate, followed by concentration. The remaining pale brown oil was purified by column chromatography to obtain 1.1 g of a pale brown amorphous solid.

Mass spectrometry confirmed that this product showed $M^+ = 694$ and was identified to be the intended product.

SYNTHESIS EXAMPLE 4

(Synthesis of Exemplary Compound 50)

Using 6.76 g of o-nitrobenzamidine in place of the 3,5-dimethylpyrazolecarboamidine in the synthesis of Exemplary Compound 30, the reaction was carried out similarly, followed by purification by column chromatography to obtain 2(o-nitrophenyl)-4-[2-(2',4'-dibromoanilino)-5-{2'-(2", 4"-di-t-amylphenoxy-i-pentanamido)}phenyl]imidazole as a reddish brown amorphous solid. Yield 8.7 g.

SYNTHESIS EXAMPLE 5

(Synthesis of Exemplary Compound 51)

In 7.0 g of the above 2-(o-nitrophenyl)-4-[2-(2',4'-dibromoanilino)-5-{2'-(2",4"-di-t-amylphenoxy-i-pentanamido)}phenyl]imidazole, 60 ml of tetrahydrofuran, 60 ml of ethanol and 0.6 g of a Pd-C catalyst were added to carry out catalytic reduction at normal pressure. The reduction was completed after about 5 days. The catalyst was removed by filtration, and the filtrate was concentrated to obtain 5.46 g of a grayish white solid.

Mass spectrometry of this product shows $M^{30} = 657$ and substantiated the structure of 2-(o-aminophenyl)-4-[2-anilino-5-{2",4"-di-t-amylphenoxy-i-pentanamido)}phenyl]imidazole.

SYNTHESIS EXAMPLE 6

(Synthesis of Exemplary Compound 52)

In 4.2 g of the above Exemplary Compound 51, 40 ml of acetonitrile was added, and 2.52 g of 2-octyloxy-5-octylbenzenesulfonyl chloride was further added, followed by stirring. In the resulting reaction mixture, 0.6 g of pyridine was added, and thereafter the reaction was carried out at room temperature for about 3 hours.

With addition of water, the reaction product was extracted with ethyl acetate. The ethyl acetate layer was washed with diluted hydrochloric acid, next with water, and further with diluted ammonia water. Thereafter it was again washed with water and dehydrated with magnesium sulfate. The ethyl acetate layer was concentrated, and the remaining viscous product was recrystallized from acetonitrile to obtain 3.78 of white crystals.

m.p.: 184° to 186° C.

SYNTHESIS EXAMPLE 7

(Synthesis of Exemplary Compound 10)

In 100 ml of ethyl acetate, 3.28 g of Exemplary Compound 52 obtained in Synthesis Exemplary 6 was dissolved, to which 0.52 g of N-chlorosuccinimide was added with stirring to effect dissolution. The reaction mixture was left to stand as it was, at room temperature for 3 weeks. Thereafter, water was added to separate an ethyl acetate layer. The ethyl acetate layer wa dehydrated and then concentrated to obtain 3.5 g of a viscous product. The product was purified by column chromatography, and the viscous product that turned 2.1 g was stood in a reduced pressure to obtain an amorphous solid.

Mass spectrometry confirmed that this product showed $M^+ = 1,071$ and was identified to be Exemplary Compound 10.

SYNTHESIS EXAMPLE 8

(Synthesis of Exemplary Compound 17)

Synthesis Example 6 was repeated to carry out the reaction, except that 0.82 g of ethyl chloroformate was used in place of 2-octyloxy-5-octylbenzenesulfonyl chloride. The reaction produce was purified by column chromatography to obtain 3.6 g of an amber viscous product. Mass spectrometry of this product showed $M^+ = 729$ and substantiated the structure of Exemplary Compound 17.

In the silver halide photographic light-sensitive material of the present invention, the cyan coupler of the present invention may preferably be added in an amount of from 10 to 200 g per mol of silver halide, which amount can be optionally varied in an appropriate range.

The coupler of the present invention can be used in combination with two or more couplers, or can be used in combination with a different type of cyan coupler.

The coupler of the present invention can be added in the silver halide photographic light-sensitive material by use of various methods such as a solid dispersion method, a latex dispersion method, and an O/W emulsifying dispersion method. For example, the O/W emulsifying dispersion method may be carried out usually by dissolving hydrophobic additives such as couplers in a high-boiling organic solvent having a boiling point of not less than about 150° C. such as tricresyl phosphate or dibutyl phthalate, optionally together with a low-boiling solvent such as ethylacetate and butyl propionate and/or water-soluble organic solvent, subjecting the resulting solution to emulsification dispersion in a hydrophilic binder such as an aqueous gelatin solution with use of a surface active agent, and thereafter adding the resulting dispersion to an intended hydrophilic colloid layer.

The silver halide photographic light-sensitive material of the present invention can be applied, for example, in color negative, positive or reversal films, and color photographic papers.

The silver halide photographic light-sensitive material of the present invention, including the color films, may have the structure that a green-sensitive emulsion layer, a red-sensitive emulsion layer and a blue-sensitive emulsion layer containing, respectively, a magenta coupler, a cyan coupler of the invention and a yellow coupler, and a non-light-sensitive layer, are laminated on a support in an appropriate layer number and layer order. The layer number and layer order, however, may be appropriately changed depending on the performance to be emphasized and the purpose for which the light-sensitive material is used.

In silver halide emulsions used in the silver halide photographic light-sensitive material of the present invention, any silver halides may be used, including silver bromide, silver iodobromide, silver iodochloride, silver chlorobromide and silver chloride, which are used in usual silver halide emulsions.

The silver halide emulsions may be chemically sensitized by the processes as exemplified by sulfur sensitization, selenium sensitization, reduction sensitization, and noble metal sensitization. The silver halide emulsions may also be optically sensitized to a desired wavelength region by using dyes known as sensitizing dyes in the field of photographic industries.

In the silver halide photographic light-sensitive material of the present invention, it is possible to optionally use anti-color-fogging agents, hardening agents, plasticizers, polymer latexes, ultraviolet absorbents, formalin scavengers, mordants, development accelerators, development restrainers, fluorescent whitening agents, matting agents, lubricants, antistatic agents, and surface active agents.

In the present invention, any processing used in the present industrial field can be carried out, as exemplified by the processing such as color developing, bleaching, fixing or bleach-fixing, stabilizing, washing, and stopping.

The silver halide photographic light-sensitive material of the present invention, which contains the novel cyan coupler, can achieve good spectral absorption characteristics of the cyan dyes formed. Namely, it shows a good sharp cut-off at the shortwave side of the absorption, less unwanted absorption at the green portion and blue portion, and superior color reproducibility. In other words, because of the high color-forming properties possessed by the cyan coupler of the present invention, it becomes possible to make films thinner to improve the image sharpness. Moreover, the thermal resistance and light-resistance of the dyes formed can be improved.

EXAMPLES

Specific examples of the present invention will be described below, but the embodiments of the present invention are by no means limited to these.

EXAMPLE 1

Based on 0.0126 mol of the cyan coupler as shown in Table 1, 3 g of dibutyl phthalate was added and 18 g of ethyl acetate was further added, thus obtaining a mixture solution. The mixture solution was heated to 60° C. and dissolved, and thereafter the resulting solution was mixed into 100 ml of an aqueous 5% gelatin solution containing 10 ml of an aqueous 5% solution of alkanol B (a trademark for an alkylnaphthalene sulfonate, available from DuPont Co.), followed by emulsifying dispersion using an ultrasonic dispersing machine to prepare a dispersion.

The above dispersion was next added in a silver iodobromide emulsion (containing 6 mol % of silver iodide) so that the cyan coupler may be 10 mol % based on the silver. In the resulting solution, 1,2-bis(vinylsulfonyl)ethane was further added as a hardening agent in a proportion of 12 mg per 1 g of gelatin, followed by coating of the solution on a transparent triacetate cellulose film support so as to give a coated silver weight of 18 mg/100 cm². Each silver halide photographic light-sensitive material thus obtained was subjected to exposure through an optical wedge according to a conventional method, and thereafter the following processing time was carried out thereon.

| Processing steps: Processing steps (38° C.) | Processing time |
| --- | --- |
| Color developing | 3 min 15 sec |
| Bleaching | 6 min 30 sec |
| Washing | 3 min 15 sec |
| Fixing | 6 min 30 sec |
| Washing | 3 min 15 sec |
| Stabilizing | 1 min 30 sec |

The processing solutions used in the processing steps had the following composition.

| (Color developing solution) | |
| --- | --- |
| 4-Amino-3-methyl-N-ethyl-N-($\beta$-hydroxyethyl)-aniline sulfate | 4.75 g |
| Anhydrous sodium sulfite | 4.25 g |
| Hydroxylamine.$\frac{1}{2}$ sulfate | 2.0 g |
| Anhydrous potassium carbonate | 37.5 g |
| Sodium bromide | 1.3 g |
| Trisodium nitrilotriacetate (monohydrate) | 2.5 g |
| Potassium hydroxide | 1.0 g |

Made up to 1 l by the addition of water, and adjusted to pH 10.0 using potassium hydroxide.

| (Bleaching solution) | |
| --- | --- |
| Ammonium ferric ethylenediaminetetraacetate | 100 g |
| Diammonium ethylenediaminetetraacetate | 10 g |
| Ammonium bromide | 150 g |
| Glacial acetic acid | 10 ml |

Made up to 1 l by the addition of water, and adjusted to pH 6.0 using ammonia water.

| (Fixing solution) | |
| --- | --- |
| Ammonium thiosulfate (an aqueous 50% solution) | 162 ml |
| Anhydrous sodium sulfite | 12.4 g |

Made up to 1 l by the addition of water, and adjusted to pH 6.5 using acetic acid.

| (Stabilizing solution) | |
| --- | --- |
| Formalin (an aqueous 37% solution) | 5.0 ml |
| Konidax (a product of Konica Corporation) | 7.5 ml |

Made up to 1 l by the addition of water.

On the silver halide photographic light-sensitive materials thus obtained, the fog, speed $S_1$, and maximum density Dmax of cyan dye images were measured.

Results obtained are shown in Table 1.

TABLE 1

| Sample No. | Coupler | Fog | $S_1$ | Dmax |
| --- | --- | --- | --- | --- |
| 1 (X) | C-1* | 0.14 | 100 | 1.45 |
| 2 (Y) | Exemplary 1 | 0.12 | 108 | 1.63 |
| 3 (Y) | Exemplary 4 | 0.13 | 107 | 1.65 |
| 4 (Y) | Exemplary 9 | 0.14 | 110 | 1.70 |
| 5 (Y) | Exemplary 29 | 0.14 | 108 | 1.68 |
| 6 (Y) | Exemplary 30 | 0.13 | 111 | 1.75 |
| 7 (Y) | Exemplary 34 | 0.11 | 113 | 1.75 |
| 8 (X) | C-2* | 0.25 | 130 | 2.10 |
| 9 (Y) | Exemplary 2 | 0.20 | 150 | 2.15 |
| 10 (Y) | Exemplary 5 | 0.23 | 163 | 2.20 |
| 11 (Y) | Exemplary 10 | 0.22 | 170 | 2.28 |
| 12 (Y) | Exemplary 18 | 0.24 | 165 | 2.25 |
| 13 (Y) | Exemplary 23 | 0.24 | 185 | 2.30 |
| 14 (Y) | Exemplary 35 | 0.23 | 160 | 2.20 |
| 15 (Y) | Exemplary 42 | 0.21 | 162 | 2.25 |

X: Comparative Example
Y: Present Invention
*Comparative coupler:

TABLE 1-continued

| Sample No. | Coupler | Fog | S₁ | Dmax |
|---|---|---|---|---|

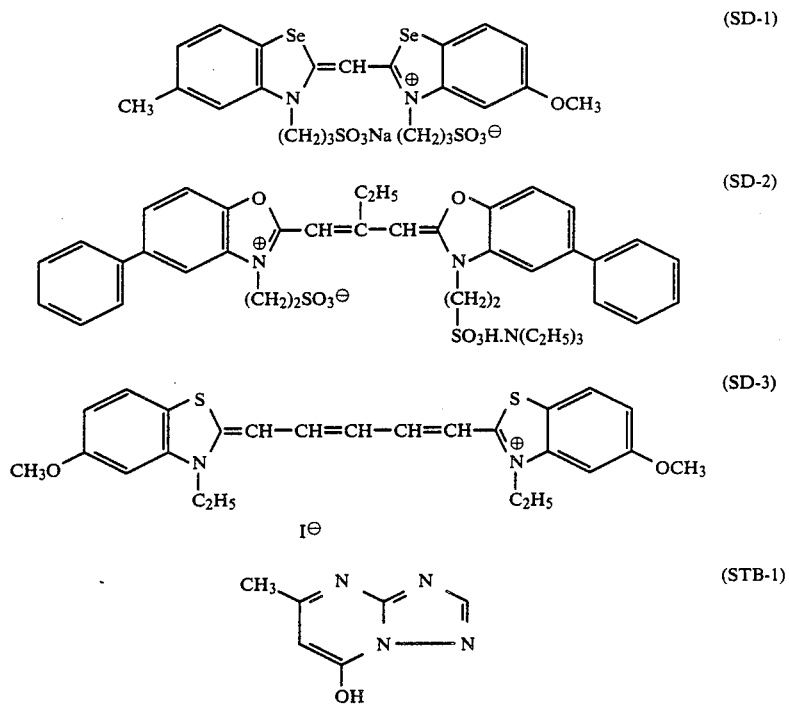

After the respective silver halide emulsions were chemically sensitized, the following STB-1 was added as an emulsion stabilizer in an amount of $5 \times 10^{-3}$ mol per mol of silver halide.

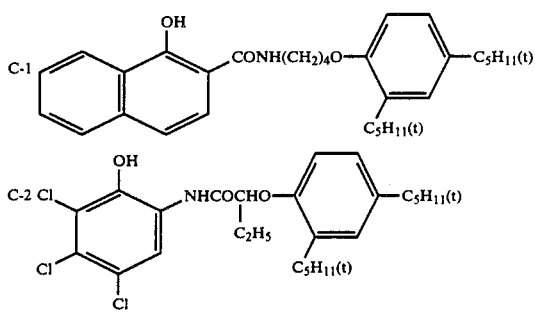

In the Table 1, inventive Samples 2 to 7 should be compared with comparative Sample 1, which samples each contain 2-equivalent groups. Samples 9 to 15 are comparable with comparative Sample 8, which samples each contain 4-equivalent couplers.

As will be evident from Table 1, all the couplers of the present invention have higher color-forming properties than the conventional couplers.

EXAMPLE 2

(Preparation of Silver Halide Emulsion)

Six kinds of silver halide emulsions as shown in Table 2 were prepared according to a neutral method and a simultaneous mixing method.

TABLE 2

| Emulsion No. | AgCl mol % | AgBr mol % | Average grain size (μm) | Chemical sensitizer | Spectral sensitizing dye |
|---|---|---|---|---|---|
| Em-1 | 99.5 | 0.5 | 0.67 | Sodium thiosulfate*¹ & chloroaurate*² | SD-1*³ |
| Em-2 | 99.5 | 0.5 | 0.46 | | SD-2*⁴ |
| Em-3 | 99.5 | 0.5 | 0.43 | | SD-3*⁵ |
| Em-4 | 10 | 90 | 0.67 | Sodium thiosulfate*¹ | SD-1*³ |
| Em-5 | 30 | 70 | 0.46 | | SD-2*⁴ |
| Em-6 | 30 | 70 | 0.43 | | SD-3*⁵ |

*¹In an amount of 2 mg per mol of silver halide.

(Preparation of Silver Halide Color Photographic Light-Sensitive Material)

Subsequently, the following Layers 1 to 7 were successively provided by coating on paper supports covered on their both sides with polyethylene, to prepare silver halide color photographic light-sensitive materials Samples 16 to 22. In the following examples, the amount for addition is indicated as an amount per 1 m² of a light-sensitive material.

Layer 1:

A layer containing 1.2 g of gelatin, 0.29 g (in terms of silver; the same applies hereinafter) of a blue-sensitive silver halide emulsion (Em-1) and 0.3 g of dinoylphthalate in which 0.75 g of a yellow coupler (Y-1), 0.3 g of a light stabilizing ST-1 and 0.015 g of 2,5-dioctylhydroquinone (HQ-1) were dissolved.

Layer 2:

A layer containing 0.9 g of gelatin of 0.2 of DOP (dioctylphthalate) in which 0.04 g of HQ-1 was dissolved.

Layer 3:

A layer containing 1.4 g of gelatin, 0.2 g of a green-sensitive silver halide emulsion (Em-2), 0.3 g of dinoylphthalate in which 0.50 g of a magenta coupler (M-1), 0.25 g of a light stabilizer (ST-2) and 0.01 g of HQ-1 were dissolved, and 6 mg of the following filter dye (AI-1).

Layer 4:

A layer containing 1.2 g of gelatin and 0.3 g of DNP in which 0.6 g of the following ultraviolet absorbent (UV-1) and 0.05 g of HQ-1 were dissolved.

Layer 5:

A layer containing 1.4 g of gelatin, 0.20 g of a red-sensitive silver halide emulsion (Em-3) and 0.3 g of DOP in which 0.9 mmol of the cyan coupler as shown in Table 3 and 0.01 g of HQ-1 were dissolved.

Layer 6:

A layer containing 1.1 g of gelatin, 0.2 g of DOP in which 0.2 g of UV-1 was dissolved, and 5 mg of the following filter dye (AI-2).

Layer 7:

A layer containing 1.0 g of gelatin and 0.05 g of sodium 2,4-dichloro-6-hydroxytriazine.

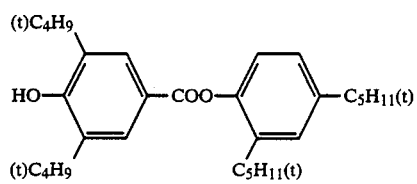 (ST-1)

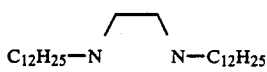 (ST-2)

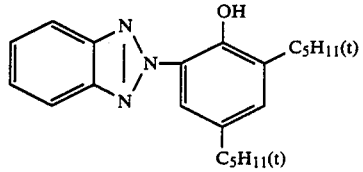 (UV-1)

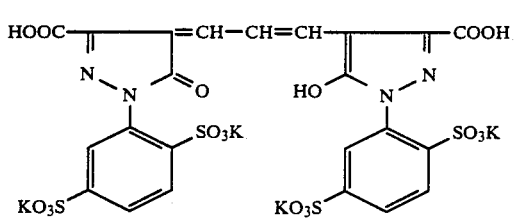 (AI-1)

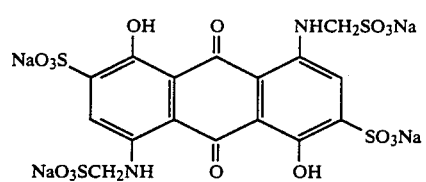 (AI-2)

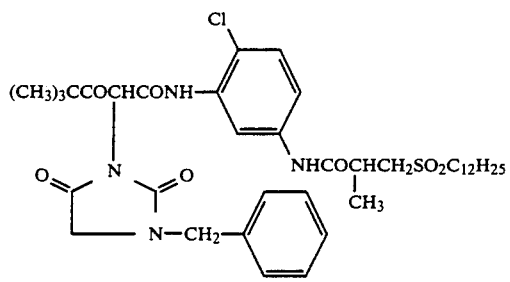 (Y-1)

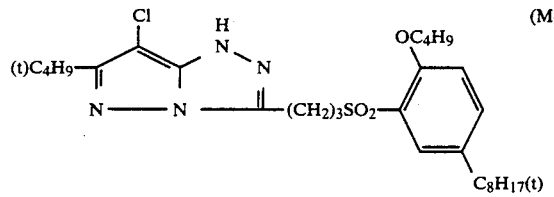 (M-1)

The samples obtained were subjected to exposure through an optical wedge, using a sensitometer Type KS-7 (available from Konica Corporation), followed by processing according to the following color developing processing steps. Thereafter, an optical densitometer Type PDA-65 (available from Konica Corporation) was used to measure the speed (a reciprocal of the amount of exposure that gives a density of fog +0.1) and maximum density (Dmax) of red-sensitive emulsion layers.

The samples obtained were also stored at 85° C. under a relative humidity of 60% for 20 days, and the remaining ratio (%) of dye images at the initial density 1.0 was determined to evaluate dark color-fading properties. Results obtained are shown in Table 3.

| Processing steps: | Temperature | Time |
|---|---|---|
| Color developing | 34.7 ± 0.3° C. | 45 sec |
| Bleach-fixing | 34.7 ± 0.3° C. | 50 sec |
| Stabilizing | 30 to 34° C. | 90 sec |
| Drying | 60 to 80° C. | 60 sec |

| (Color developing solution) | |
|---|---|
| Pure water | 800 ml |
| Triethanolamine | 8 g |
| N,N-diethylhydroxylamine | 5 g |
| Potassium chloride | 2 g |
| N-ethyl-N-β-methanesulfonamidoethyl-3-methyl-4-aminoaniline sulfate | 5 g |
| Sodium tetrapolyphosphate | 2 g |
| Potassium carbonate | 30 g |
| Potassium sulfite | 0.2 g |
| Fluorescent whitening agent (a 4,4'-diaminostilbenedisulfonic acid derivative) | 1 g |

Made up to 1 l in total amount by the addition of pure water, and adjusted to pH 10.2.

| (Bleach-fixing solution) | |
|---|---|
| Ammonium ferric ethylenediaminetetraacetate dihydrate | 60 g |
| Ethylenediaminetetraacetic acid | 3 g |
| Ammonium thiosulfate (a 70% solution) | 100 ml |
| Ammonium sulfite (a 40% solution) | 27.5 ml |

Made up to 1 l in total amount by the addition of water, and adjusted to pH 5.7 using potassium carbonate or glacial acetic acid.

| (Stabilizing solution) | |
|---|---|
| 5-Chloro-2-methyl-4-isothiazolin-3-on | 1 g |
| 1-Hydroxyethylidene-1,1-diphosphonic acid | 2 g |

Made up to 1 l by the addition of water, and adjusted to pH 7.0 using sulfuric acid or potassium hydroxide.

TABLE 3

Comparative coupler (C-3)

| Sample No. | Coupler | Speed* | Dmax | Remaining ratio of color image |
|---|---|---|---|---|
| 16 (X) | C-2 | 100 | 2.55 | 80% |

TABLE 3-continued

Comparative coupler (C-3)

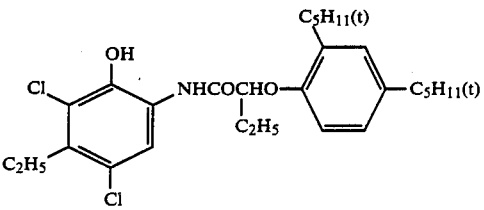

| Sample No. | Coupler | Speed* | Dmax | Remaining ratio of color image |
|---|---|---|---|---|
| 17 (X) | C-3 | 97 | 2.55 | 92 |
| 18 (Y) | Exemplary 10 | 115 | 2.63 | 94 |
| 19 (Y) | Exemplary 18 | 110 | 2.66 | 95 |
| 20 (Y) | Exemplary 35 | 112 | 2.65 | 94 |
| 21 (Y) | Exemplary 37 | 110 | 2.61 | 96 |
| 22 (Y) | Exemplary 38 | 108 | 2.62 | 95 |

X: Comparative Example
Y: Present Invention
*The speed is indicated by a relative value, assuming the speed of Sample 16 as 100.

As is evident from Table 3, a high maximum density and a high speed can be obtained and also the resulting cyan images have a good thermal resistance, when the cyan couplers of the present invention are used.

The color reproducibility was also visually evaluated on the samples obtained by printing the above Samples 16, 17, 20, 21, 22 through color negatives obtained by photographing Color Checker (available from Macbeth Co.) using Konicolor GX-100 under conditions adjusted so that the image of neutral color portion of Color Checker is reproduced to neutral color on the printed samples.

When compared with Samples 16 to 17, Samples 20, 21 and 22, which are in accordance with the present invention, have been remarkably improved in the distinction between blue and cyan and the color reproducibility of green and red to magenta.

EXAMPLE 3

Example 2 was entirely repeated to prepare silver halide photographic light-sensitive materials Samples 23 to 29, except that the blue-sensitive silver halide emulsion used in Layer 1, the green-sensitive silver halide emulsion used in Layer 3 and the red-sensitive silver halide emulsion used in Layer 5 were respectively replaced with Em-4, Em-5 and Em-6 shown in Table 2.

The samples obtained were subjected to exposure through an optical wedge, using a senitometer Type KS-7 (manufactured by Konica Corporation), followed by processing according to the following color development processing steps. Thereafter the same measurement as Example 2 was made.

Results obtained are shown in Table 4.

| (Processing steps) | | |
|---|---|---|
| Color developing | 3 min 30 sec | Temp: 33° C. |
| Bleaching | 1 min 30 sec | Temp: 33° C. |
| Washing | 3 min | Temp: 33° C. |

| Color developing solution | |
|---|---|
| N-ethyl-N-β-methanesulfonamidoethyl-3-methyl-4-aminoaniline sulfate | 4.9 g |
| Hydroxylamine sulfate | 2.0 g |
| Potassium carbonate | 25.0 g |
| Potassium bromide | 0.6 g |
| Anhydrous sodium sulfite | 2.0 g |
| Benzylalcohol | 13 ml |
| Polyethylene glycol (average degree of polymerization: 400) | 3.0 ml |

Made up to 1 l by the addition of water, and adjusted to pH 10.0 using sodium hydroxide.

| Bleach-fixing solution | |
|---|---|
| Sodium ferric ethylenediaminetetraacetic acid | 6.0 g |
| Ammonium thiosulfate | 100 g |
| Sodium bisulfite | 10 g |
| Sodium metabisulfite | 3 g |

Made up to 1 l by the addition of water, and adjusted to pH 7.0 using ammonia water.

TABLE 4

| Sample No. | Coupler | Speed* | Dmax | Remaining ratio of color image |
|---|---|---|---|---|
| 23 (X) | C-2 | 100 | 2.50 | 81% |
| 24 (X) | C-3 | 101 | 2.52 | 91 |
| 25 (Y) | Exemplary 10 | 118 | 2.68 | 93 |
| 26 (Y) | Exemplary 18 | 113 | 2.66 | 92 |
| 27 (Y) | Exemplary 35 | 110 | 2.70 | 94 |
| 28 (Y) | Exemplary 37 | 115 | 2.71 | 95 |
| 29 (Y) | Exemplary 38 | 117 | 2.68 | 95 |

X: Comparative Example
Y: Present Invention
*The speed is indicated by a relative value, assuming the speed of Sample 23 as 100.

EXAMPLE 4

The following emulsion were prepared.
Preparation of Emulsion S:

A 2.0% inert gelatin solution (750 ml) was maintained at 50° C., and the following Solutions A1 and B were simultaneously added therein with stirring, which were poured into it taking 3 minutes. After ripening for 25 minutes, excessive salts were removed by precipitation washing. The resulting flocculate was redispersed, followed by addition of solutions C1 to D1. After 10 minutes, excessive water-soluble salts were again removed, a small amount of gelatin was added, and then the silver halide particles were dispersed.

Preparation of Emulsion L:

A 1.5% inert gelatin solution (750 ml) was maintained at 60° C., and the following Solution A2 and B were simultaneously added therein with stirring, which were poured into it taking 15 minutes. After ripening for 40 minutes, excessive salts were removed by precipitation washing. The resulting flocculate was redispersed, and 10 mg of sodium thiosulfate was added, followed by addition of Solutions C2 and D2. After 10 minutes, excessive water-soluble salts were again removed, a small amount of gelatin was added, and then the silver halide particles were dispersed.

Preparation of Emulsion M:

A 2.0% insert gelatin solution (750 ml) was maintained at 50° C., and the following Solutions A3 and B were simultaneously added therein with stirring, which were poured into it taking 5 minutes. After ripening for 25 minutes, excessive salts were removed by precipitation followed by addition of Solutions C1 and D2. After 10 minutes, excessive water-soluble salts were again removed, a small amount of gelatin was added, and then the silver halide particles were dispersed.

| Solution A1: | |
|---|---|
| Pure water | 2,000 ml |
| NaCl | 35 g |
| NH$_4$Br | 109.6 g |
| KI | 0.8 g |
| Solution A2: | |
| Pure water | 1,000 ml |
| NaCl | 26.3 g |
| NH$_4$Br | 109.6 g |
| KI | 0.8 g |
| Solution A3: | |
| Pure water | 1,000 ml |
| NaCl | 33.8 g |
| KBr | 12 g |
| Solution B: | |
| Pure water | 1,200 ml |
| AgNO$_3$ | 170 g |
| Solution C1: | |
| Pure water | 1,000 ml |
| NaCl | 60 g |
| NH$_4$Br | 6.9 g |
| Solution C2: | |
| Pure water | 1,000 ml |
| NaCl | 31.6 g |
| Solution D1: | |
| Pure water | 1,000 ml |
| AgNO$_3$ | 70 g |
| Solution D2: | |
| Pure water | 1,000 ml |
| AgNO$_3$ | 80 g |

IN the above three types of emulsions, sensitizing dyes, couplers and so forth were added in the following way. The resulting solutions were coated on a support to prepare a multi-layer color light-sensitive material.

Red-sensitive emulsion layer (First layer):

To Emulsions S and M, respectively, added were sensitizing dyes (PD-3) and PD-4), stabilizers (STB-1) and (STB-2), a surface active agent (S-2), and further a protectively dispersed coupler solution containing dibutyl phthalate, ethyl acetate, a surface active agent (S-2) 2,5-dioctylhydroquinone and cyan couplers (C-2) and (C-4).

Gelatin was added. The respective emulsions were mixed, and the resulting mixed emulsion was coated so that a gamma value of 1.5 may be given.

First intermediate layer (Second layer):

A gelatin solution containing a protectively dispersed solution containing dioctyl phthalate, 2,5-dioctylhydroquinone, an ultraviolet absorbent Tinubin 328 (available from Ciba Geigy Corp.) and a surface active agent (S-1) was prepared, and coated so that Tinubin may be in a coating weight of 0.15 g/m$^2$.

Green-sensitive emulsion layer (Third layer):

To Emulsions S and M, respectively, added were a sensitizing dye (PD-2), stabilizers (STB-1) and (STB-2), a surface active agent (S-2), and further a protectively dispersed coupler solution containing dibutyl phthalate, ethyl acetate, 2,5-dioctylhydroquinone, a surface active agent (S-1), and a magenta coupler (M-2).

Gelatin was added, and a hardening agent (H-1) was further added. The resulting mixed emulsion was coated so that a gamma value of 1.5 may be given.

Second intermediate layer (Fourth layer):

With the same formulation with the first intermediate layer, the solution was coated so that Tinubin 328 may be in a coating weight of 0.2 g/m$^2$.

Yellow filter layer (Fifth layer):

To an yellow colloidal silver solution prepared by reduction in the presence of an alkaline weakly reducing agent (after neutralization, the weakly reducing agent was removed by noodle washing method), a solution comprising dioctyl phthalate, ethyl acetate, a surface active agent (S-1), and 2,5-dioctylhydroquinone, a surface active agent (S-2) and a hardening agent (H-1) were added. The resulting solution was coated so that the colloidal silver may be in a coating weight of 0.15 g/m$^2$.

Third intermediate layer (Sixth layer):

The same as the first intermediate layer.

Blue-sensitive emulsion layer (Seventh layer):

To Emulsions L, S and M, respectively, added were a sensitizing dye (PD-1), stabilizers (STB-1) and (STB-3), a surface active agent (S-2), and further a protectively dispersed coupler solution containing dibutyl phthalate, ethyl acetate, 2,5-dioctylhydroquinone, a surface active agent (S-1), and a yellow coupler (Y-2). Gelatin was added, and a hardening agent (H-1) was further added. The resulting emulsions were mixed and coated so that a gamma value of 1.5 may be given.

Third intermediate layer (Eighth layer):

With the same formulation as the first intermediate layer, the solution was coated so that Tinubin 328 may be in a coating weight ob 0.2 g/m$^2$.

Protective layer (Ninth layer):

A gelatin solution containing colloidal silica, a surface active agent (S-2) and hardening agents (H-2) and (H-3) was coated so that the gelatin may be in a coating weight of 1.0 g/m$^2$.

On a polyethylene-laminated paper having been subjected to surface treatment, the first layer to the ninth layer were provided by a simultaneous coating method, followed by drying (Sample 30).

Samples 31 to 33 were further prepared in the same manner except that the cyan coupler used in the red-sensitive layer (the first layer) was replaced with equimolar amounts of the couplers of the present invention as shown in Table 5.

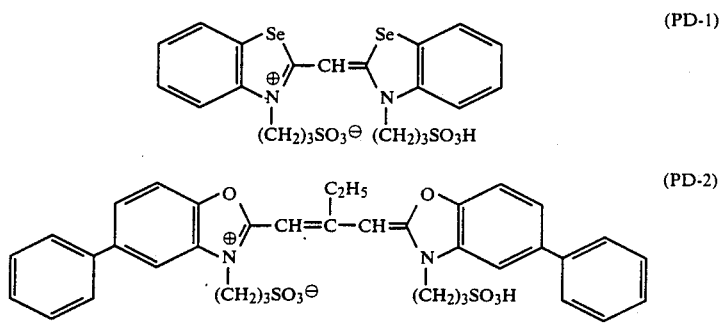

-continued
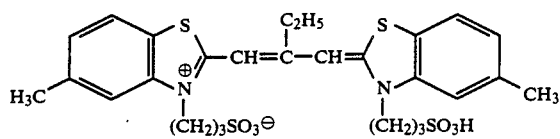 (PD-3)
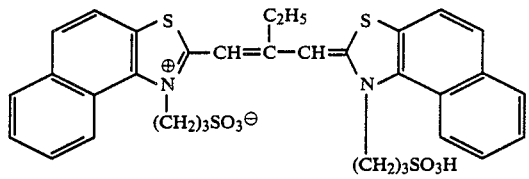 (PD-4)
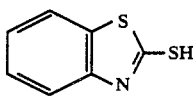 (STB-2)
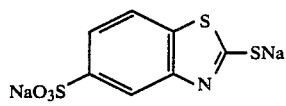 (STB-3)
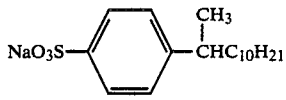 (S-1)
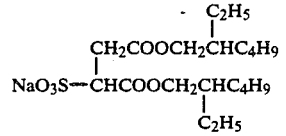 (S-2)
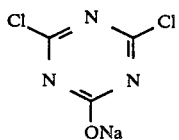 (H-1)
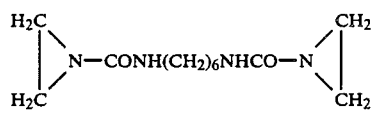 (H-2)
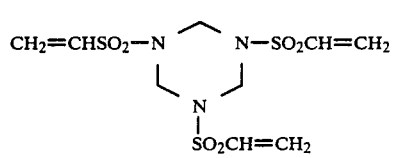 (H-3)
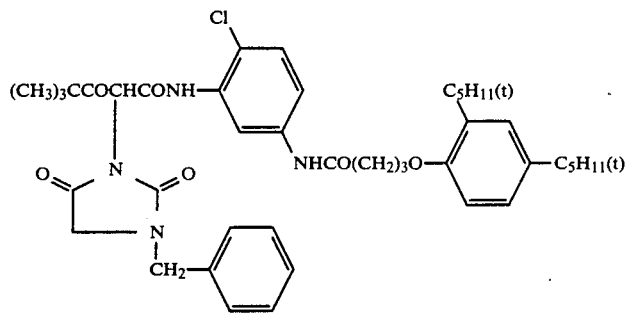 (Y-2)

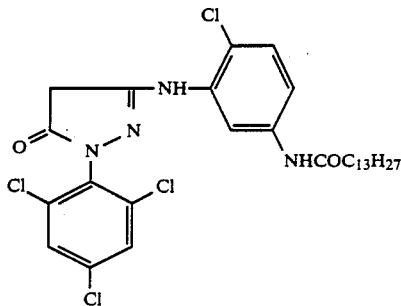
(M-2)

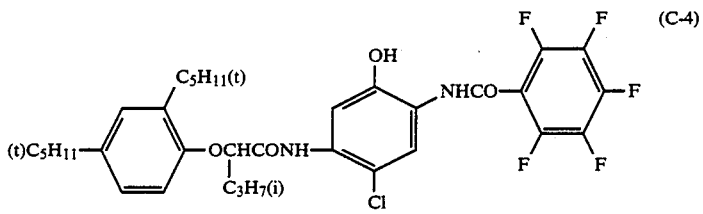
(C-4)

The light-sensitive materials Samples 30 to 33 prepared in the above way were subjected to exposure to white light through an optical wedge, and then development processing according to the following steps to obtain neutral color positive images of the wedge.

The Dmax of the resulting cyan images was measured. Also measured was the retention of cyan images at the density 1.0 observed when the images were stored at 85° C. under a relative humidity of 60% for 20 days. Results obtained are shown in Table 5.

Processing steps: (Processing temperature and processing time)

| [1] | Immersing in color developing solution | 38° C. | 8 sec |
|---|---|---|---|
| [2] | Fogging exposure | — | 10 sec under 1 lux |
| [3] | Color developing | 38° C. | 2 min |
| [4] | Bleach-fixing | 35° C. | 60 sec |
| [5] | Stabilizing | 25 to 30° C. | 1 min 30 sec |
| [6] | Drying | 75 to 80° C. | 1 min |

Composition of processing solutions:

(Color developing solution)

| Benzyl alcohol | 10 ml |
|---|---|
| Ethylene glycol | 15 ml |
| Potassium sulfite | 2.0 g |
| Potassium bromide | 1.5 g |
| Sodium chloride | 0.2 g |
| Potassium carbonate | 30.0 g |
| Hydroxylamine sulfate | 3.0 g |
| Polyphosphoric acid (TPPS) | 2.5 g |
| 3-Methyl-4-amino-N-ethyl-N-(β-methanesulfonamidoethyl) aniline sulfate) | 5.5 g |
| Fluorescent whitening agent (a 4,4'-diaminostilbenedisulfonic acid derivative) | 1.0 g |
| Potassium hydroxide | 2.0 g |

Made up to 1 l in total amount by the addition of water, and adjusted to pH 10.20.

(Bleach-fixing solution)

| Ammonium ferric ethylenediaminetetraacetate dihydrate | 60 g |
|---|---|
| Ethylenediaminetetraacetic acid | 3 g |
| Ammonium thiosulfite (a 70% solution) | 100 ml |
| Ammonium sulfite (a 40% solution) | 27.5 ml |

Made up to 1 l in total amount by the addition of water, and adjusted to pH 7.1 using potassium carbonate or glacial acetic acid.

(Stabilizing solution)

| 5-Chloro-2-methyl-4-isothiazolin-3-on | 1.0 g |
|---|---|
| Ethylene glycol | 10 g |
| 1-Hydroxyethylidene-1,1'-diphosphonic acid | 2.5 g |
| Bismuth chloride | 0.2 g |
| Magnesium chloride | 0.1 g |
| Ammonium hydroxide (an aqueous 28% solution) | 2.0 g |
| Sodium nitrilotriacetate | 1.0 g |

Made up to 1 l in total amount by the addition of water, and adjusted to pH 7.0 using ammonium hydroxide or sulfuric acid.

The stabilizing was carried out using a countercurrent system comprised of two tanks.

TABLE 5

| Sample No. | Coupler | Dmax | Remaining rate |
|---|---|---|---|
| 30 (X) | C-2 C-4 | 2.24 | 88% |
| 31 (Y) | Exemplary 10 | 2.41 | 94 |
| 32 (Y) | Exemplary 18 | 2.35 | 95 |
| 33 (Y) | Exemplary 35 | 2.30 | 95 |

X: Comparative Example
Y: Present Invention

As is shown above, the couplers of the present invention are seen to have a good thermal resistance. The above light-sensitive materials were each loaded on Konicolor 7 (manufactured by Konica Corporation), and Color Checker (available from Macbeth Co.) was copied by scanning exposure at a constant rate of 5 cm/sec from a rectangular slit of 1×20 cm. As a result, Samples 31 to 33 showed distinct differences in the hue between cyan and blue, and more improved color reproducibility of green and red to magenta, than the comparative Sample 30.

EXAMPLE 5

On a triacetyl cellulose film support having been applied with antistatic treatment at its back surface and subjected to subbing using a copolymer of maleic anhydride with vinyl acetate on the surface of the support to be coated with emulsion, the respective layers having the following composition were provided by coating from the support side to prepare a multi-layer color light-sensitive material Sample 34. The amount for addition is indicated as an amount per mol of silver halide unless particularly mentioned.

| (Back surface antistatic treatment) | |
|---|---|
| Back surface layer 1: | |
| Stearic acid | 20 mg/m$^2$ |
| Diacetyl cellulose | 10 mg/m$^2$ |
| Alumina sol | 1 g/m$^2$ |
| Back surface layer 2: | |
| Diacetyl cellulose | 50 mg/m$^2$ |
| Stearic acid | 10 mg/m$^2$ |
| Silica matting agent (average particle diameter: 3 μm) | 50 mg/m$^2$ |
| (On the emulsion coating surface) | |
| First layer: Anti-halation layer | |
| Ultraviolet absorbent UV-2 | 0.3 g/m$^2$ |
| Ultraviolet absorbent UV-3 | 0.4 g/m$^2$ |
| Black colloidal silver | 0.24 g/m$^2$ |
| Gelatin | 2.7 g/m$^2$ |
| Second layer: Intermediate layer | |
| 2,5-Di-t-octylhydroquinone | 0.1 g/m$^2$ |
| Gelatin | 1.0 g/m$^2$ |
| Third layer: Low-speed red-sensitive silver halide emulsion layer | |
| Monodisperse emulsion comprising AgBrI having an average grain size of 0.35 μm and containing 12.5 mol % of AgI (Emulsion I) | 0.5 g/m$^2$ in silver weight |
| Sensitizing dye 1 | 7.6 × 10$^{-4}$ mol |
| Coupler C-5 | 0.1 mol |
| Gelatin | 0.9 g/m$^2$ |
| Fourth layer: High-speed red-sensitive silver halide emulsion layer | |
| Monodisperse emulsion comprising AgBrI having an average grain size of 0.75 μm and containing 12.5 mol % of AgI (Emulsion II) | 0.8 g/m$^2$ in silver weight |
| Sensitizing dye 1 | 3.2 × 10$^{-4}$ mol |
| Coupler C-5 | 0.2 mol |
| Gelatin | 1.75 g/m$^2$ |
| Fifth layer: Intermediate layer | |
| 2,5-Di-t-octylhydroquinone | 0.1 g/m$^2$ |
| Gelatin | 0.9 g/m$^2$ |
| Sixth layer: Low-speed green-sensitive silver halide emulsion layer | |
| Emulsion I | 1.0 g/m$^2$ in silver weight |
| Sensitizing dye 2 | 6.6 × 10$^{-4}$ mol |
| Sensitizing dye 3 | 0.6 × 10$^{-4}$ mol |
| Coupler M-3 | 0.05 mol |
| Gelatin | 0.8 g/m$^2$ |
| Seventh layer: High-speed green-sensitive silver halide emulsion layer | |
| Emulsion II | 1.0 g/m$^2$ in silver weight |
| Sensitizing dye 2 | 2.76 × 10$^{-4}$ mol |
| Sensitizing dye 3 | 0.23 × 10$^{-4}$ mol |
| Coupler M-3 | 0.15 mol |
| Gelatin | 1.5 g/m$^2$ |
| Eight layer: Intermediate layer | |
| The same as the fifth layer. | |
| Ninth layer: Yellow filter layer | |
| Yellow colloidal silver | 0.1 g/m$^2$ |
| Gelatin | 0.9 g/m$^2$ |
| 2,5-Di-t-octylhydroquinone | 0.1 g/m$^2$ |
| Tenth layer: Low-speed blue-sensitive silver halide emulsion layer | |
| Monodisperse emulsion comprising AgBrI having an average grain size of 0.6 μm and containing 12.5 mol % of AgI (Emulsion III) | 0.4 g/m$^2$ in silver weight |
| Spectrally sensitizing dye 4 | 2.65 × 10$^{-4}$ mol |
| Coupler Y-3 | 0.3 mol |
| Gelatin | 1.3 g/m$^2$ |
| Eleventh layer: High-speed blue-sensitive silver halide emulsion layer | |
| Monodisperse emulsion comprising AgBrI having an average grain size of 1.0 μm and containing 12.5 mol % of AgI (Emulsion IV) | 0.8 g/m$^2$ in silver weight |
| Spectrally sensitizing dye 4 | 1.59 × 10$^{-4}$ mol |
| Coupler Y-3 | 0.3 mol |
| Gelatin | 2.1 g/m$^2$ |
| Twelfth layer: First protective layer | |
| UV-2 | 0.3 g/m$^2$ |
| UV-3 | 0.4 g/m$^2$ |
| Gelatin | 1.2 g/m$^2$ |
| 2,5-Di-t-octylhydroquinone | 0.1 g/m$^2$ |
| Thirteenth layer: Second protective layer | |
| Non-light-sensitive fine grain silver halide emulsion comprising AgBrI having an average grain size of 0.106 μm and containing 1 mol % of AgI | 0.3 g/m$^2$ in silver weight |
| Polyethyl ethacrylate particles | (diameter: 1.5 μm) |
| Gelatin | 0.7 g/m$^2$ |
| Surface active agent S-3 | |

In each layer, H-1and surface active agents were also added in addition to the above composition. Tricresyl phosphate was also used as a coupler solvent.

All the emulsions were monodisperse octahedral emulsions, obtained by making a seed emulsion of 0.095 μm or 0.25 μm (average silver iodide content: 2 mol %) grow according to a double-jet process in which the pAg and pH are controlled at 45° C. in the presence of ammonia. The silver iodide contents in the core, intermediate layer and shell were controlled by changing the composition of the silver halide to be added.

In making the silver halide emulsion of a core/shell type grow, used were the methods as disclosed in Japanese Patent O.P.I. Publications No. 52238/1984, No. 138538/1985, No. 49938/1983 and No. 122935/1985. Compounds used in preparing the samples were as follows:

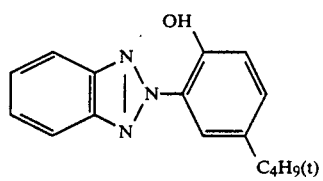

Ultraviolet absorbent UV-2

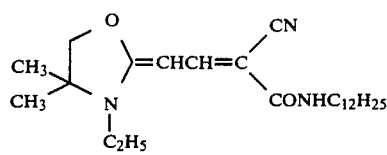

Ultraviolet absorbent UV-3

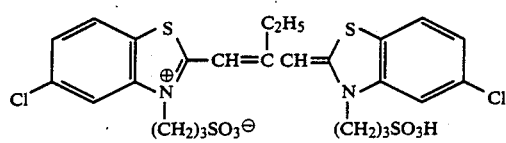

Sensitizing dye 1

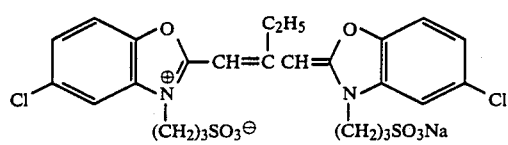

Sensitizing dye 2

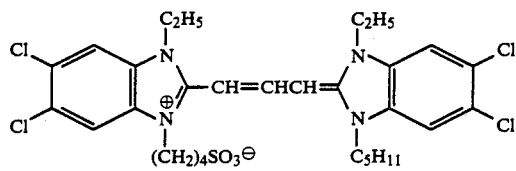

Sensitizing dye 3

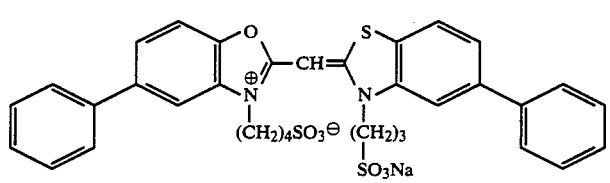

Sensitizing dye 4

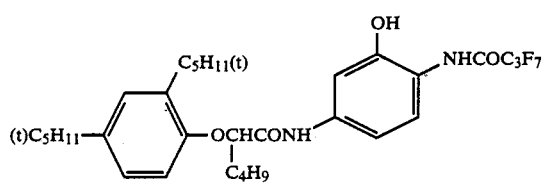

Coupler C-5

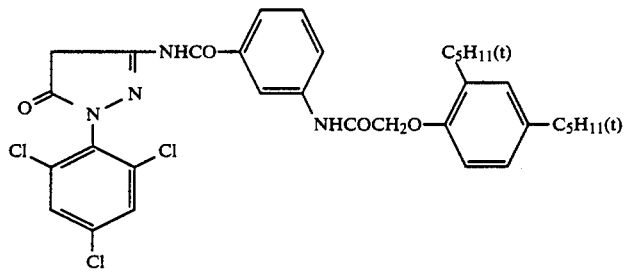

Coupler M-3

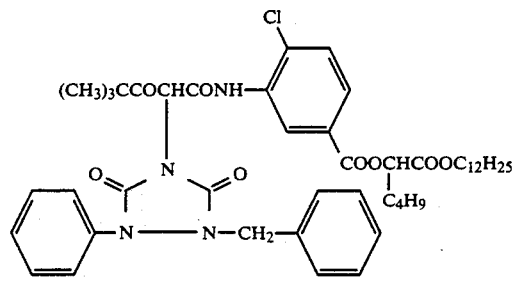

Coupler Y-3

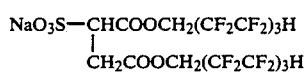

Surface active agent 1

Light-sensitive materials were next prepared in which the cyan couplers used in the third layer and fourth layer of Sample 34 were replaced with Couplers 1, 4, 9 and 34 and the total weight of the third layer and fourth layer was reduced 30%, which were designated as Samples 35, 36, 37 and 38, respectively.

Samples 34 to 38 were subjected to wedge exposure and the following reversal processing. Thereafter the Dmax of cyan images were measured under red light. Samples 34 to 38 were actually used to photograph a color checker (available from Macbeth Co.), followed by reversal processing. Thereafter the color reproducibility was visually compared.

Results obtained are shown in Table 6.

| Processing steps | Processing time | Processing temperature |
|---|---|---|
| First developing | 6 min | 38° C. (± 0.3) |
| Washing | 2 min | 38° C. (± 0.3) |
| Reversing | 2 min | 38° C. (± 0.3) |
| Color developing | 6 min | 38° C. (± 0.3) |
| Compensating | 2 min | 38° C. (± 0.3) |
| Bleaching | 6 min | 38° C. (± 0.3) |
| Fixing | 4 min | 38° C. (± 0.3) |
| Washing | 4 min | 38° C. (± 0.3) |
| Stabilizing | 1 min | Room temp. |
| Drying | | |

| First developing solution | |
|---|---|
| Water | 700 ml |
| Sodium tetrapolyphosphate | 2 g |
| Sodium sulfite | 20 g |
| Hydroquinone monosulfonate | 30 g |
| Sodium carbonate (monohydrate) | 30 g |
| 1-Phenyl-4-methyl-4-hydroxymethyl-3-pyrazolidone | 2 g |
| Potassium bromide | 2.5 g |
| Potassium thiocyanate | 1.2 g |
| Potassium iodide (a 0.1% solution) | 2 ml |

Made up to 1,000 ml by the addition of water.

| Reversing solution | |
|---|---|
| Water | 700 ml |
| Hexasodium nitrilotrimethylene phosphonate | 3 g |
| Stannous chloride (dihydrate) | 1 g |
| p-Aminophenol | 0.1 g |
| Sodium hydroxide | 8 g |
| Glacial acetic acid | 15 ml |

Made up to 1,000 ml by the addition of water.

| Color developing solution | |
|---|---|
| Sodium tetrapolyphosphate | 2 g |
| Sodium sulfite | 7 g |
| Sodium tertiary phosphate (dihydrate) | 36 g |
| Potassium bromide | 1 g |
| Potassium iodide (a 0.1% solution) | 90 ml |
| Sodium hydroxide | 3 g |
| Citrazinic acid | 1.5 g |
| N-methyl-N-(β-methanesulfonamidoethyl)-3-methyl-4-aminoaniline sulfate | 11 g |
| Ethylenediamine | 3 g |

Made up to 1,000 ml by the addition of water.

| Compensating solution | |
|---|---|
| Water | 700 ml |
| Sodium sulfite | 12 g |
| Sodium ethylenediaminetetraacetate (dihydrate) | 8 g |
| Thioglycerol | 0.4 ml |
| Glacial acetic acid | 3 ml |

Made up to 1,000 ml by the addition of water.

| Bleaching solution | |
|---|---|
| Sodium ethylenediaminetetraacetate (dihydrate) | 2.0 g |
| Ammonium ferric ethylenediaminetetraacetate (dihydrate) | 120.0 g |

| -continued | |
|---|---|
| Bleaching solution | |
| Ammonium bromide | 100.0 g |

Made up to 1,000 ml by the addition of water.

| Fixing solution | |
|---|---|
| Water | 800 ml |
| Ammonium thiosulfate | 80.0 g |
| Sodium sulfite | 5.0 g |
| Sodium bisulfite | 5.0 g |

Made up to 1,000 ml by the addition of water.

| Stabilizing solution | |
|---|---|
| Water | 800 ml |
| Formalin (37 wt. %) | 5.0 ml |
| Konidax (a product of Konica Corporation) | 5.0 ml |

Made up to 1,000 ml by the addition of water.

TABLE 6

| Sample No. | Coupler | Dmax* |
|---|---|---|
| 34 (X) | C-5 | 3.10 |
| 35 (Y) | Exemplary 1 | 3.26 |
| 36 (Y) | Exemplary 4 | 3.25 |
| 37 (Y) | Exemplary 9 | 3.23 |
| 38 (Y) | Exemplary 34 | 3.24 |

*Measured by red light
X: Comparative Example
Y: Present Invention

As will be seen from the above results, the samples of the present invention show Dmax more than the same as the comparative sample because of the higher molar absorptivity coefficient, even though the coating weights of the third layer and fourth layer are reduced.

As far as those on which Color Checker was actually photographed were visually evaluated, Samples 35 to 38 of the present invention also show a good distinction between cyan and blue, which is a feature of the coupler of the present invention, and show an improved color reproducibility of green and red.

EXAMPLE 6

Silver halide emulsions prepared by the procedures as disclosed in Japanese Patent Application No. 31330/1983, which are core/shell silver iodobromide emulsions having a multi-shell structure such that iodine content becomes lower from the iodine-rich inner shell in the inside of a grain toward the outer side layer, were chemically sensitized according to a conventional method. Coating solutions comprising the following additives were coated on a triacetyl cellulose film support successively from the support side to prepare a color light-sensitive material Sample 39 comprised of 13 layers.

First layer: Anti-halation layer
A gelatin layer containing black colloidal silver.
Gelatin: 1.2 g/m².

Second layer: Intermediate layer
A gelatin layer containing an emulsified dispersion of 2,5-di-t-octylhydroquinone.
Gelatin: 1.2 g/m².

Third layer: Low-speed red-sensitive silver halide emulsion layer

Monodisperse emulsion comprising octahedral silver iodobromide having an average grain size of 0.38 μm and an average iodine content of 7.84% (in weight ratio) (Emulsion I): 1.8 g/m² in silver coating weight.

Sensitizing dye 5: $6\times10^{-5}$ mol per mol of silver.
    Sensitizing dye 6: $1.0\times10^{31\ 5}$ mol per mol of silver.
    Sensitizing dye 7: $1.0\times10^{-5}$ mol per mol of silver.
    Cyan coupler (C-6): 0.06 mol per mol of silver.
    Colored cyan coupler (CC-1): 0.003 mold per mol of silver.
    DIR Compound (D-1): 0.0015 mol per mol of silver.
    DIR Compound (D-2): 0.002 mol per mol of silver.

Fourth layer: High-speed red-sensitive silver halide emulsion layer

Monodisperse emulsion comprising octahedral silver iodobromide having an average grain size of 0.65 μm and an average iodine content of 7.37% in weight ratio (Emulsion II): 1.3 g/m² in silver coating weight.

Sensitizing dye 5: $3\times10^{31\ 5}$ mol per mol of silver.
    Sensitizing dye 6: $1.0\times10^{-5}$ mol per mol of silver.
    Sensitizing dye 7: $1.0\times10^{-5}$ mol per mol of silver.
    Cyan coupler (C-6): 0.02 mol per mol of silver.
    Colored cyan coupler (CC-1): 0.0015 mol per mol of silver.
    DIR Compound (D-2): 0.001 mol per mol of silver.
    Gelatin: 1.0 g/m².

Fifth layer: Intermediate layer

The same gelatin layer as the second layer.
    Gelatin: 1.0 g/m².

Sixth layer: Low-speed green-sensitive silver halide emulsion layer

Emulsion I: 1.5 g/m² in silver coating weight.
    Sensitizing dye 8: $2.5\times10^{-5}$ mol per mol of silver.
    Sensitizing dye 9: $1.2\times10^{-5}$ mol per mol of silver.
    Sensitizing dye b 10: $1.0\times10^{-5}$ mol per mol of silver.
    Magenta coupler (M-4): 0.05 mol per mol of silver.
    Colored magenta coupler (CM-1): 0.009 mol per mol of silver.
    DIR Compound (D-1): 0.0010 mol per mol of silver.
    DIR Compound (D-3): 0.0030 mol per mol of silver.
    Gelatin: 2.0 g/m².

Seventh layer: High-speed green-sensitive silver halide emulsion layer

Emulsion II: 1.4 g/m² in silver coating weight.
    Sensitizing dye 8: $1.5\times10^{-5}$ mol per mol of silver.
    Sensitizing dye 9: $1.0\times10^{-5}$ mol per mol of silver.
    Sensitizing dye 10: $7.0\times10^{-5}$ mol per mol of silver.
    Magenta coupler (M-4): 0.020 mol per mol of silver.
    Colored magenta coupler (CM-1): 0.002 mol per mol of silver.
    DIR Compound (D-3): 0.0010 mol per mol of silver.
    Gelatin: 1.8 g/m².

Eighth layer: Intermediate layer

The same gelatin layer as the second layer.
    Gelatin: 1.0 g/m².

Ninth layer: Yellow filter layer

A gelatin layer containing yellow colloidal silver and an emulsification dispersion of 2,5-di-t-octylhydroquinone.
    Gelatin: 1.5 g/m².

Tenth layer: Low-speed blue-sensitive silver halide emulsion layer

Monodisperse emulsion (Emulsion I): 0.9 g/m² in silver coating weight.
    Sensitizing dye 11: $1.3\times10^{-5}$ mol per mol of silver.
    Yellow coupler (Y-4): 0.29 mol per mol of silver.
    Gelatin: 1.9 g/m².

Eleventh layer: High-speed blue-sensitive silver halide emulsion layer

Monodisperse emulsion (Emulsion II): 0.5 g/m² in silver coating weight.
    Sensitizing dye 11: $1.0\times10^{-5}$ mol per mol of silver.
    Yellow coupler (Y-4): 0.08 mol per mol of silver.
    DIR compound (D-2): 0.0015 mol per mol of silver.
    Gelatin: 1.6 g/m².

Twelvth layer: First protective layer

A gelatin layer containing:
    silver iodobromide (AgI: 1 mol %; average grain size: 0.07 μm): 0.5 g/m² in silver coating weight; and
    ultraviolet absorbents UV-1 and UV-3.
    Gelatin: 1.2 g/m².

Thirteenth layer: Second protective layer (Pro-2)

A gelatin layer containing; polymethyl methacrylate particles (diameter: 1.5 μm); particles of an ethyl methacrylate/methyl methacrylate/methacrylic acid copolymer (average particles diameter: 2.5 μm); polydimethylsiloxane: 5 mg/m²;

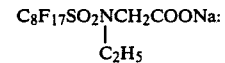

10 mg/m²; and a formalin scavenger (HS-1).
    Gelatin: 1.2 g/m².

In each layer, a gelatin hardening agent (H-1) and a surface active agent were added in addition to the above composition.

(Additives)

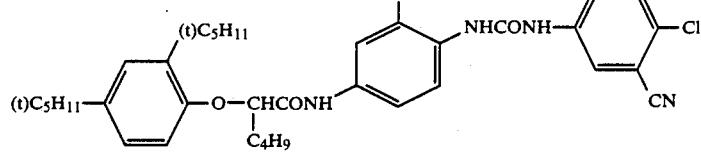

C-6

-continued
(Additives)
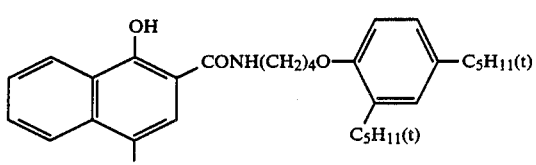
CC-1
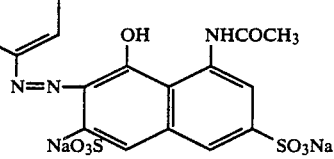
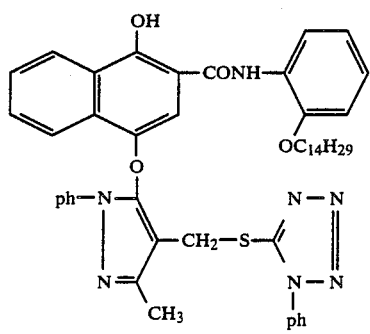
D-1
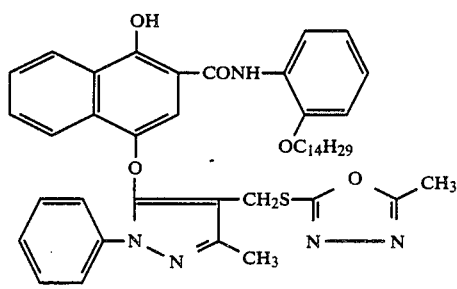
D-2
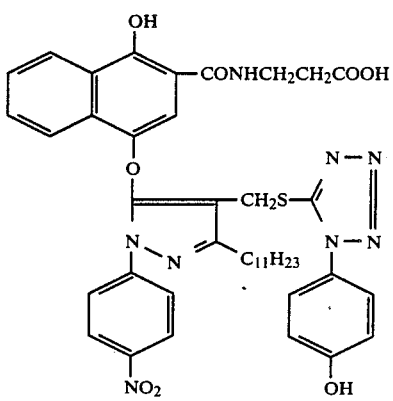
D-3
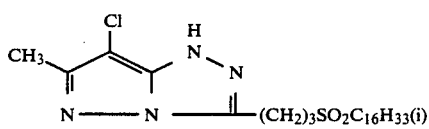
M-4

(Additives)
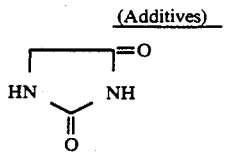
HS-1
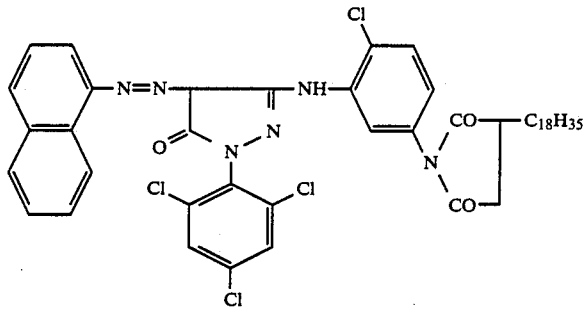
CM-1
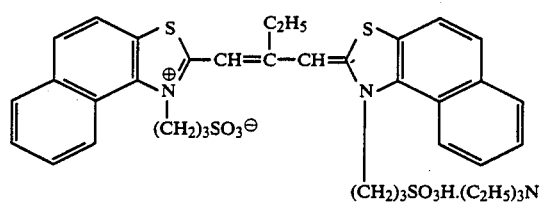
Sensitizing dye 5
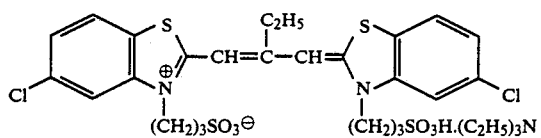
Sensitizing dye 6
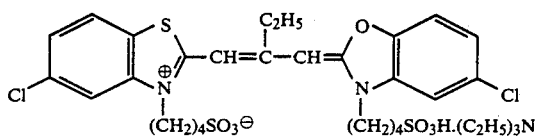
Sensitizing dye 7
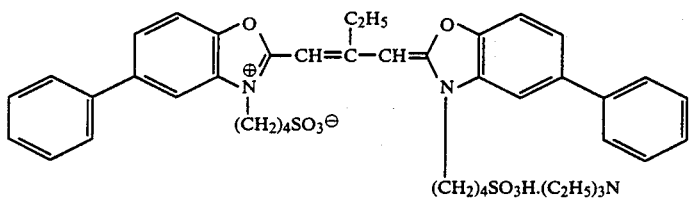
Sensitizing dye 8
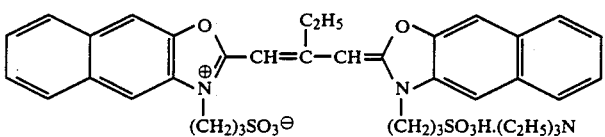
Sensitizing dye 9
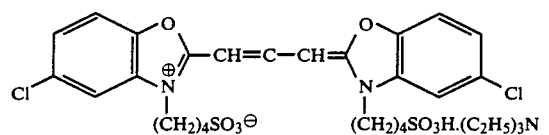
Sensitizing dye 10
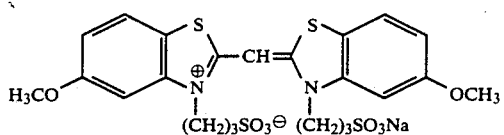
Sensitizing dye 11

(Additives)

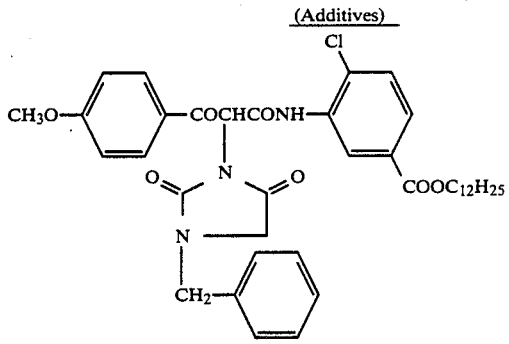

Y-4

Light-sensitive materials were obtained by replacing the cyan couplers used in the third layer and fourth layer, with the couplers 4, 5, 9 and 16 of the present invention as shown in Table 7, used in an amount 0.6 molar time the amount of the comparative coupler, and were designated as Samples 40, 41, 42 and 43.

The samples prepared in this way were subjected to wedge exposure using white light, the following development processing was carried out, and then the speed and fog of panchromatic layers were determined. The speed was indicated by a logarithm of the amount of exposure that gives a density of fog +0.5, and shown as a relative value, assuming the speed of Sample 39 as 100.

Cyan images were also stored at 85° C. under a relative humidity of 60% for 20 days, where the retention after deterioration, at the density 1.0 was measured.

Results obtained are shown together in Table 7.

| Processing steps: (38° C.) | |
|---|---|
| Color developing | 3 min 15 sec |
| Bleaching | 6 min 30 sec |
| Washing | 3 min 15 sec |
| Fixing | 6 min 30 sec |
| Washing | 3 min 15 sec |
| Stabilizing | 1 min 30 sec |
| Drying | |

Processing solutions used in the respective processing steps had the following composition.

| (Color developing solution) | |
|---|---|
| 4-Amino-3-methyl-N-ethyl-N-($\beta$-hydroxyethyl) aniline sulfate | 4.75 g |
| Anhydrous sodium sulfite | 4.25 g |
| Hydroxylamine $\frac{1}{2}$ sulfate | 2.0 g |
| Anhydrous potassium carbonate | 37.5 g |
| Sodium bromide | 1.3 g |
| Trisodium nitrilotriacetate (monohydrate) | 2.5 g |
| Potassium hydroxide | 1.0 g | made up to 1 l by the addition of water.

| (Bleaching solution) | |
|---|---|
| Ammonium ethylenediaminetetraacetate | 100.0 g |
| Diammonium ethylenediaminetetraacetate | 10.0 g |
| Ammonium bromide | 150.0 g |
| Glacial acetic acid | 10.0 ml |

Made up to 1 l by the addition of water, and adjusted to pH 6.0 using ammonia water.

| (Fixing solution) | |
|---|---|
| Ammonium thiosulfate | 175.0 g |
| Anhydrous sodium sulfite | 8.5 g |
| Sodium metasulfite | 2.3 g |

Made up to 1 l by the addition of water, and adjusted to pH 6.0 using acetic acid.

| (Stabilizing solution) | |
|---|---|
| Formalin (an aqueous 37% solution) | 1.5 ml |
| Konidax (a product of Konica Corporation) | 7.5 ml |

Made up to 1 l by the addition of water.

TABLE 7

| Sample No. | Coupler | Speed | Remaining ratio |
|---|---|---|---|
| 39 (X) | C-6 | 100 | 80% |
| 40 (Y) | Exemplary 4 | 118 | 91 |
| 41 (Y) | Exemplary 6 | 120 | 94 |
| 42 (Y) | Exemplary 9 | 120 | 93 |
| 43 (Y) | Exemplary 16 | 128 | 90 |

X: Comparative Example
Y: Present Invention

These results tell that the samples in which the couplers of the present invention are used can give a higher speed and have a superior thermal resistance irrespective of the smaller amount of couplers than that of the comparative sample.

What is claimed is:

1. A silver halide photographic light-sensitive material comprising a support and provided thereon a silver halide emulsion layer containing a cyan coupler represented by the following formula I:

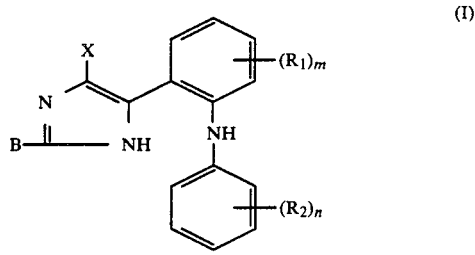

(I)

wherein B is an organic group comprising a carbon atom, nitrogen atom, oxygen atom or sulfur atom directly bonded to the imidazole ring; $R_1$ and $R_2$ each are a substituent; m is an integer of 0 to 4, n is an integer of 0 to 5, provided that the groups represented by said $R_1$ or $R_2$ are respectively allowed to be the same with or different from each other when m or n is 2 or more,; and X is a group capable of being split off upon coupling reaction with the oxidation product of a color developing agent.

2. The material of claim 1, wherein said substituent represented by $R_1$ or $R_2$ is a halogen atom, a cyano group a nitro group, a carboxy group, an alkyl group, an alkoxy group, a carbamoyl group, a sulfamoyl group, an acyl group, an acyloxy group, an alkoxycarbonyl group, an alkylamido group, an arylamido group, an alkylsulfonamido group, an arylsulfonamido group, a dialkylcarbamoylamino group, an alkoxycarbonylamino group, an aryloxycarbonylamino group or a sulfamoylamino group.

3. The material of claim 1, wherein said organic group represented by B is an alkyl group, an aryl group, a heterocyclic group, a cyano group, a carboxyl group, an acyl group, a carbamoyl group, an alkoxycarbonyl group, an aryloxycarbonyl group, an acylamino group, alkoxycarbonylamino group, aryloxycarbonylamino group, a sulfonamido group, an anilino group, a ureido group, a sulfamoylamino group, an amino group, an alkoxy group, an aryloxy group, a silyloxy group, a heterocyclic oxy group, an alkythio group, an arylthio group or a heterocyclic thio group, these groups may have a substituent.

4. The material of claim 3, wherein said group represented by B is a

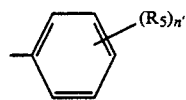

group,

group or a $-LR_8$ groups, wherein $R_5$, $R_6$, $R_7$ and $R_8$ are each a substituent; L is an oxygen atom or a sulfur atom, n' is an integer of from zero to 5, provided that the groups represented by said $R_6$ and $R_7$ are allowed to bond to form a ring and groups represented by $R_5$ may be the same with or different from each other when n' is 2 or more.

5. The material of claim 4, wherein said group represented by B is

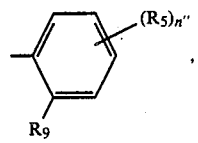

wherein $R_9$ is a an amino group, an alkylamino group, an arylamino group, an alkylamido group, an arylamido group, an alkylsulfonamido group, an arylsulfonamido group, dialkylcarbamoylamino group, alkoxycarbonylamino group, an aryloxycarbonylamino group or a sulfamoylamino group; and n" is an integer of zero to 4.

6. The material of claim 1, said cyan coupler is contained in said silver halide emulsion layer in an amount of from 10 g to 300 g per mol of silver halide contained said emulsion layer.

* * * * *